US009198884B2

(12) United States Patent
Malmsten et al.

(10) Patent No.: US 9,198,884 B2
(45) Date of Patent: Dec. 1, 2015

(54) USE OF CARBOXYMETHYLCELLULOSE TO CONTROL EJECTABILITY AND SOLIDIFICATION TIME OF COMPOSITIONS COMPRISING ONE OR MORE BIORESORBABLE CERAMICS

(75) Inventors: Lars Åke Malmsten, Lund (SE); Niklas Axén, Järlåsa (SE); Hans Lennernäs, Uppsala (SE); Anders Carlsson, Stockholm (SE)

(73) Assignee: LIDDS AB, Helsingborg (SE)

( * ) Notice: Subject to any disclaimer, the term of this patent is extended or adjusted under 35 U.S.C. 154(b) by 166 days.

(21) Appl. No.: 13/127,331

(22) PCT Filed: Nov. 27, 2009

(86) PCT No.: PCT/EP2009/008496
§ 371 (c)(1),
(2), (4) Date: May 27, 2011

(87) PCT Pub. No.: WO2010/060644
PCT Pub. Date: Jun. 3, 2010

(65) Prior Publication Data
US 2011/0223214 A1     Sep. 15, 2011

(30) Foreign Application Priority Data

Nov. 27, 2008  (DK) ................................ 2008 01674

(51) Int. Cl.
| A61K 9/14 | (2006.01) |
| A61K 31/167 | (2006.01) |
| A61K 31/57 | (2006.01) |
| A61K 31/277 | (2006.01) |
| A61K 9/00 | (2006.01) |
| A61K 47/02 | (2006.01) |
| A61K 47/38 | (2006.01) |
| A61L 27/44 | (2006.01) |
| A61L 27/58 | (2006.01) |

(52) U.S. Cl.
CPC ............. *A61K 31/167* (2013.01); *A61K 9/0019* (2013.01); *A61K 31/57* (2013.01); *A61K 47/02* (2013.01); *A61K 47/38* (2013.01); *A61L 27/446* (2013.01); *A61L 27/58* (2013.01); *A61L 2400/06* (2013.01)

(58) Field of Classification Search
CPC .... A61L 2400/06; A61K 47/02; A61K 47/38; A61K 9/0019
See application file for complete search history.

(56) References Cited

U.S. PATENT DOCUMENTS

| 3,891,453 | A | 6/1975 | Williams |
| 4,114,384 | A | 9/1978 | Kennedy-Skipton |
| 4,814,336 | A | 3/1989 | Szentmiklosi et al. |
| 6,652,887 | B1 * | 11/2003 | Richelsoph et al. .......... 424/549 |
| 2003/0050710 | A1 | 3/2003 | Petersen et al. |
| 2003/0235621 | A1 | 12/2003 | Miller et al. |
| 2006/0205652 | A1 | 9/2006 | Zamora et al. |
| 2006/0283356 | A1 | 12/2006 | Donlon et al. |
| 2009/0036392 | A1 | 2/2009 | Lennernas et al. |
| 2009/0118215 | A1 | 5/2009 | Lennernas et al. |

FOREIGN PATENT DOCUMENTS

| EP | 1 208 850 A1 | 5/2002 |
| EP | 2 116 233 A1 | 11/2009 |
| GB | 999487 A | 7/1965 |
| JP | 56-26756 A | 3/1981 |
| JP | 2000-264710 A | 9/2000 |
| WO | WO 2004/000334 A1 | 12/2003 |
| WO | WO2004000334 A1 * | 12/2003 |
| WO | WO 2004/108625 A1 | 12/2004 |
| WO | WO 2005/039537 A1 | 5/2005 |
| WO | WO 2007/104549 A2 | 9/2007 |
| WO | WO 2007104549 A2 * | 9/2007 |

OTHER PUBLICATIONS

International Search Report (PCT/ISA/210) issued on Apr. 19, 2010, by European Patent Office as the International Searching Authority for International Application No. PCT/EP2009/008496.
Written Opinion (PCT/ISA/237) issued on Apr. 19, 2010, by European Patent Office as the International Searching Authority for International Application No. PCT/EP2009/008496.
International Preliminary Report on Patentability (PCT/IPEA/416) issued on May 13, 2011 in corresponding International Application No. PCT/EP2009/008496.
Lewis, K.N., et al., "Use of Carbomethylcellulose to Improve the Mechanical and Handling Characteristics of Clacium Sulfate Bone Graft Material," *Proceedings of the Second Joint EMBS/BMES Conference*—Houston, Texas, USA Oct. 23-26, 2002, pp. 444-445, Institute of Electrical and Electronics Engineers (2002).

* cited by examiner

*Primary Examiner* — Kyle Purdy
(74) *Attorney, Agent, or Firm* — Sterne, Kessler, Goldstein & Fox P.L.L.C.

(57) ABSTRACT

Carboxymethylcellulose, notably sodium carboxymethylcellulose or other alkali metal or alkaline earth metal salts of carboxymethylcellulose, are employed to control solidification time of compositions comprising one or more bioresorbable ceramics, notably a hydratable calcium sulphate, in order to facilitate preparation of a ready-to-use composition for inserting into the body by injection.

23 Claims, No Drawings

USE OF CARBOXYMETHYLCELLULOSE TO CONTROL EJECTABILITY AND SOLIDIFICATION TIME OF COMPOSITIONS COMPRISING ONE OR MORE BIORESORBABLE CERAMICS

FIELD OF THE INVENTION

The present invention relates to the use of carboxymethylcellulose, notably sodium carboxymethylcellulose or other alkali metal or alkaline earth metal salts of carboxymethylcellulose, to control solidification time of compositions comprising one or more bioresorbable ceramics, notably a hydratable calcium sulphate, in order to facilitate preparation of a ready-to-use composition for inserting into the body by injection. Notably, the present invention provides compositions having a specific range of weight ratios between the amount of carboxymethylcellulose (expressed as sodium carboxymethylcellulose) and the amount of a hydratable bioresorbable ceramic (expressed as calcium sulphate hemihydrate) in a ready-to-use composition. Moreover, the present invention provides compositions that have suitable properties for handling of the compositions before, during and after administration into a mammal, notably a human. Thus, before administration, a ready-to-use composition is easily prepared by mixing a composition comprising one or more bioresorbable ceramics with a liquid comprising the sodium carboxymethylcellulose. The ready-to-use composition obtained must have a viscosity that is neither too high (which would make the ready-to-use composition impossible to administer via injection) nor too low (which would cause difficulties in obtaining a homogeneous dispersion of the hydratable bioresorbable ceramic), i.e. use of sodium carboxymethylcellulose imparts sufficient viscosity, excellent dispersability and moreover, leads to a solidification time that is balanced between the need to handling the ready-to-use composition as a liquid composition before administration and a relatively fast solidification after the ready-to-use composition has been administered to the target site and, if necessary, is suitably spread at the target site. After administration the ready-to-use composition must solidify at such a rate that the composition stays at the administered injection site. A too long solidification time may result in the composition being distributed in an uncontrolled way. Due to the internal pressure being formed in the organ to which the ready-to-use composition according to present invention is administered to it will be necessary to have a relatively short solidification time of the composition to avoid displacement of the composition e.g. out of the injection hole/site.

BACKGROUND

Ceramics have for many years been used for local applications, e.g. as bone void filler in clinical settings or in different forms of drug delivery systems for controlled and/or targeted delivery therapy. Many of the ceramics used are bioresorbable (or biodegradable) and various ceramics based on calcium salts, such as calcium phosphate or calcium sulphate systems, have been described. These ceramics are often referred to as hydratable or hydrating ceramics due to their ability to react chemically with water to solidify by forming hydrates. Some hydrating ceramics are considered stable in a biological environment, e.g. hydroxylapatite and calcium silicates The bioresorbable ceramics have many favourable properties for use as implants or in controlled release applications in pharmaceutical formulations compared to e.g. polymers (such as polylactic acids and poly(lactic-co-glycolic-acids)) by their biocompatibility and bioresorbability. In general, the bioresorbable ceramics are non-toxic and are based on molecules which normally occur in the living tissues of mammals. Calcium sulphate is particularly attractive since it is a resorbable and biocompatible material, i.e. it disappears over time.

In general a composition is prepared by mixing hydratable ceramic, such as calcium sulphate, with water and e.g. a medicament or a bone matrix to provide a paste to be implanted as such or in a solid form. To minimize surgery, it is desirable to inject the paste into the body or organ through a small size cannula. However, mixing calcium sulphate and water results in a rapid onset of solidification, which reduces the time that the surgeon has to apply the paste before it solidifies, and also makes it difficult in praxis to eject the paste through a small sized cannula. In order to minimize the surgical intervention it is desirable to achieve a composition which has a prolonged solidification time, and an enhanced ejectability from a small sized cannula, whereby the composition can be implanted into the body without surgery, or with minimal surgery only.

The aim of the present invention is to make a composition that is injectable through a small cannula into the body of a subject, and which composition has a prolonged solidification time.

The inventors found this achievable by using a composition comprising an aqueous solution of carboxymethylcellulose, notably the sodium salt (Na-CMC), calcium sulphate hemihydrate ($CaSO_4 \cdot \frac{1}{2}H_2O$), and, optionally particles of calcium sulphate dihydrate ($CaSO_4 \cdot 2H_2O$).

Na-CMC is commonly used as thickener, binder, stabilizer, and suspending agent in various forms of compositions. However, the inventors of the present invention have found it possible to control three important parameters of a composition by small adjustments of the Na-CMC concentration; namely the miscibility of the calcium sulphate hemihydrate powder with water; the ejectability of the formed paste through a thin needle, cannula, and/or biopsy cannula; and the retardation of the solidification time of the paste.

An important aspect of this composition is that Na-CMC is in an aqueous form before it is mixed with $CaSO_4 \cdot \frac{1}{2}H_2O$. As Na-CMC is slowly soluble in water, the aqueous form may be obtained by mixing Na-CMC with water, stirring this mixture for a few hours. The aqueous solution of completely dissolved Na-CMC is then mixed with $CaSO_4 \cdot \frac{1}{2}H_2O$ just before use of the resulting paste. Optionally, the aqueous solution of Na-CMC can be sterilized by autoclaving and possibly also by sterile filtration, if the viscosity is not too high. Na-CMC is considered to be completely dissolved in a medium when a clear transparent thermodynamically stable solution is observed.

In addition, Na-CMC may also be provided in dry form, preferably as a thin film or a freeze-dried powder. In any event, if Na-CMC or another carboxymethylcellulose is used it is important to ensure that the carboxymethylcellulose relatively fast dissolves. Normally, Na-CMC has a relatively slow dissolution rate, which means that the properties of Na-CMC cannot be utilized within the 5-15 min available from establishment of the ready-to-use composition and to the injection and solidification of the composition. Accordingly, if carboxymethylcellulose is employed in dry form it should be either in form of micronized powder, lyophilized powder or as a thin film. Another possibility could be to incorporate a wetting agent in the composition, provided that such an agent does not have any negative impact on the ready-to-use composition.

By doing this, the inventors have achieved a composition that enables them to control the solidification time and also enables injection from a small needle in a syringe. Further, it has been found that this composition is retaining an acceptable miscibility. In addition, the composition does not require any addition of acid or acidic solution, such as aqueous acetic acid, to control the solidification time.

In US 2006/205652 is disclosed a composition in the form of a paste, gel or liquid for the delivery of synthetic heparin-binding growth factor analogues for bone or cartilage repair. In some aspects of the invention the composition can comprise a calcium sulphate compound and Na-CMC (gelling agent). However, the calcium sulphate compositions disclosed in the examples are not in hydratable form as calcium sulphate dihydrate is employed. Furthermore, in the examples disclosed a surfactant in (Pluronic) is being used in the solutions of Na-CMC.

EP1208850 discloses an osteogenesis promoter sustained-release paste that comprises an osteogenesis promoter, a calcium component and a viscosity-increasing agent. There are no examples showing a ready-to-use composition containing a hydratable calcium sulphate ceramic (e.g. calcium sulphate hemihydrate) and Na-CMC.

In WO 2007/104549 is disclosed a highly densified composition comprising e.g. calcium sulphate in the form of a calcium sulphate hemihydrate and a gelling or swelling agent which may include Na-CMC for the treatment of benign prostate hyperplasia. However, there are no examples showing a ready-to-use composition containing a hydratable calcium sulphate ceramic with Na-CMC only examples in which methylcellulose is used together with acetic acid.

In WO 2004/000334 is described a bone graft substitute composition which may comprise calcium sulphate, a mixing solution such as sterile water and a plasticizing material. However, no examples are given of a combination of Na-CMC and calcium sulphate.

JP56026756 discloses and discusses a method for producing alpha gypsum hemihydrate including carboxymethylcellulose under high pressure to result in a dry alpha gypsum hemihydrate. The solidification times disclosed are in the order of 1 hour or more and it is furthermore an object of JP56026756 to present gypsum structures having a light weight structure (porous bubble inclusion) with very high stability in the order of 6 months or more in water. However there is no disclosure of any method or composition according to present invention as is not an object of present invention to produce dry $CaSO_4.\frac{1}{2}H_2O$ containing carboxymethylcellulose.

Thus, to the best of the inventors knowledge, no one have described a composition comprising Na-CMC, calcium sulphate hemihydrate and, optionally, sulphate dihydrate which, by specific adjustments of the Na-CMC concentration in the composition, gives a good miscibility of the calcium sulphate hemihydrate powder with an aqueous medium (e.g. water), an acceptable ejectability of the formed paste through a thin needle, and sufficient retardation of the solidification time of the paste to allow handling and administration of the ready-to-use composition without unnecessary prolongation of the solidification to avoid inappropriate spreading or clearance from the administration site.

DETAILED DESCRIPTION OF THE INVENTION

In the present invention is described a pharmaceutical composition comprising a mixture of calcium sulphate and carboxymethylcellulose which gives rise to a prolonged solidification time, while at the same time is able to retain an acceptable miscibility of the formed paste, as well as an acceptable ejectability through a syringe with a small cannula.

In particular the composition comprises calcium sulphate hemihydrate and the sodium salt of carboxymethylcellulose (Na-CMC). The inventors have found that by small adjustments of the amount of Na-CMC added to such a composition it is possible to control the solidification process of calcium sulphate hemihydrate (i.e. $CaSO_4.\frac{1}{2}H_2O \rightarrow CaSO_4.2H_2O$). Furthermore, the viscosity is enhanced by addition of Na-CMC and thus improves the ejectability from a syringe with a small sized needle/cannula.

It is also envisaged that other salts of carboxymethylcellulose can be employed in present invention such as, e.g., alkali metal (Li, K, Na), or alkaline earth metals (Ca, Mg, Sr) of carboxymethylcellulose, provided they are water-soluble and acceptable for injection into a mammal, notably a human.

Furthermore, the inventors have surprisingly found that a composition comprising fully hydrated calcium sulphate hemihydrate (i.e. calcium sulphate dihydrate) and Na-CMC is reliably ejectable through the orifice of a syringe optionally having a cannula of size such as e.g. 6 G, 8 G, 9 G, 10 G, 11 G 12 G, 13 G, 14 G, 16 G, 19 G, 20 G, 21 G, 22 G, 23 G, 24 G, and 26 G. This implies that Na-CMC not only acts as a curing retardant, a viscosity modifier but also has a dispersing effect, wherein Na-CMC proves to be particularly useful as an additive in e.g. therapeutic use for administration of compositions by cannula or thin tubing. In the context of a medical application this is particularly important as this feature of Na-CMC will allow a precise amount of composition to be administered without risking an interrupted procedure due to partial curing of the composition resulting in an interrupted administration.

The solidification time and the ejectability are two very important parameters for a surgeon when implanting said composition into the body of a subject. By changing the amount of Na-CMC in form of an aqueous solution, added to the composition it is possible by the surgeon to adjust the solidification within a suitable time frame (e.g. 5-15 minutes) that allows sufficient time to properly apply the composition before it becomes solid. At the same time it is possible to apply the composition through a thin needle (e.g. 15 G or thinner) due to the ejectability of the compositions. The ejectability thus enables the surgeon to apply the composition into the body or organ without surgery, or with minimal invasive surgery only. As the time for 100% solidification may be difficult to measure, the present inventors apply a measure for ejectability in order to evaluate the solidification properties of a composition of the invention. Thus, in the present context, in some instances the time for solidification is regarded to be the time, when the composition can no longer be ejected from a specific syringe. In other instances the mixture may not have solidified but may not be ejectable. The test is described in detail herein.

A further advantage of using aqueous solutions of Na-CMC (or other salts of carboxymethylcellulose, cf. above) as a diluent for calcium sulphate hemihydrate is that it provides good dispersability, which affects the miscibility of the calcium sulphate hemihydrate with water.

The present inventors have found that the amount of carboxymethylcellulose employed is important for the above-mentioned characteristic, especially it is possible to obtain a suitable balance of solidification time, ejectability, dispersability and viscosity when carboxymethylcellulose (or a salt thereof, notably Na-CMC) is used in a narrow concentration window expressed as a weight ratio between the carboxymethylcellulose (expressed as Na-CMC) and calcium sulphate hemihydrate in the final ready-to-use composition.

Also mixtures of sodium carboxymethylcellulose and methylcellulose are of interest to the invention. Additions of methylcellulose are made to increase the viscosity of the diluents without affecting the ejectability time.

In the present context, the term "ready-to-use" composition is used to denote a composition obtained by admixing a first component comprising a composition with a hydratable calcium sulphate, notably calcium sulphate hemihydrate, with a second component comprising an aqueous solution of carboxymethylcellulose (or a salt thereof, notably Na-CMC). The ready-to-use composition is in liquid form, i.e. it is in a transient form where the hydratable calcium sulphate is taking up water from the aqueous medium to convert the hemisulphate to fully or partially hydrated calcium sulphate (i.e. fully hydrated calcium sulphate is calcium sulphate dihydrate) and thereby changing the composition from a liquid composition to a solid composition. The transient form may be regarded as a paste, i.e. a viscous suspension. However, the existence of the ready-to-use composition in liquid form must last for a sufficient period of time that enable the medical personnel to ensure a proper mixing of the two components and to allow for administration of the ready-to-use composition all within at least about 5 to at the most about 15 minutes.

On the other hand, the time for solidification of the ready-to-use composition must not be too long. It is important that the ready-to-use composition reaches the target within the body (e.g. by administration directly into the target organ) and at that site solidifies. Another important aspect is that if the solidification time is too long, there is a risk that the composition will start to pour out of the injection site/hole which will lead to an inexact dosing of the active ingredient. A certain spreading out of the composition at the target site may be desirable in order to distribute the composition in the target organ, but if the solidification time becomes too long, a risk will arise with respect to undesired clearance from the target organ and possible transport of the composition to unwanted sites within the body, where it then solidifies.

Calcium sulphate dihydrate acts as an accelerator to the hydration (solidification) of calcium sulphate hemihydrates. Therefore compositions containing mixtures of calcium sulphate hemihydrates and calcium sulphate dihydrate solidifies very rapidly and an efficient retarder is necessary. This is an important aspect of the present invention as some compositions disclosed herein have a pharmaceutical active ingredient mixed with particles of calcium sulphate dihydrate.

In the present context, a suitable solidification time is from about 5 min to about 15 min, or longer such as e.g. from about 5 min to about 20 min. In specific cases, dependent on the target organ in question, longer solidification times may be useful. However, it is not expected that a solidification time of more than 1 hour is suitable. Thus the solidification time may be from about 5 min to about 25 min, such as from about 5 min to about 30 min, such as from about 5 min to about 35 min, such as from about 5 min to about 40 min, such as from about 5 min to about 45 min, such as from about 5 min to about 50 min or from about 5 min to about 1 hour, after admixing the above-mentioned components (i.e. calcium hemisulphate, a Na-carboxymethylcellulose dissolved in an aqueous medium and calcium sulphate dihydrate). The decisive point in time is when the ready-to-use composition no longer can be delivered via a syringe equipped with a 15 G needle, or any other appropriate needle size, such as 17 G (17 G=1.5 mm outer diameter and 1.3 mm inner diameter) or 18 G (18 G=1.3 outer diameter and 1.0 mm inner diameter). Other needle sizes that may be of importance in use of compositions according to present invention are such as e.g. 6 G, 8 G, 9 G, 10 G, 11 G 12 G, 13 G, 14 G, 16 G, 19 G, 20 G, 21 G, 22 G, 23 G, 24 G, and 26 G. As discussed hereinbefore, the ejectability time may differ from solidification time as a ready-to-use paste may not have solidified but may still be impossible to eject. Therefore, in the present context, the solidification time is determined by measuring the point in time, where a ready-to-use composition cannot be delivered via a specific orifice of a syringe (as described in details herein).

In the present context the term "hydration" refers to the chemical process of transforming e.g. calcium sulphate hemihydrate to calcium sulphate dihydrate. The hydration process is typically started by adding an aqueous medium to the calcium sulphate hemihydrate and depending on the amount of water added and the amount of calcium sulphate hemihydrate, the hydration may be partly or fully. In the present context, the term "partly hydrated" is intended to denote a ceramic, wherein the amount of aqueous medium added corresponds to at least about 20% of the stoichiometric amount necessary to hydrate the one or more hydratable and bioresorbable ceramics, whereas the term "fully hydrated" is intended to denote a ceramic, wherein the amount of aqueous medium added corresponds to at the most about 90%, such as e.g. at the most 95%, at the most about 99%, or at the most 100% of the stoichiometric amount necessary to hydrate the one or more hydratable and bioresorbable ceramics.

Ejectability

In the present context, the term "ejectability" of a composition is intended to mean the composition in a syringe being able to pass through the orifice of the syringe optionally equipped with a cannula or needle of size such as e.g. 6 G, 8 G, 9 G, 10 G, 11 G 12 G, 13 G, 14 G, 16 G, 19 G, 20 G, 21 G, 22 G, 23 G, 24 G, 25 G or 26 G or flexible tubing. In the present context the ejectability is tested by admixing an aqueous solution of Na-CMC and $CaSO_4$ (hemihydrate optionally together with dihydrate that may further be compacted) in the amounts as described herein, placing the resulting mixture in a plastic syringe and ejecting the mixture/slurry by hand. The mixture/slurry is considered to be ejectable when there is no clogging or obstruction of the mixture preventing it from passing through the orifice by moderate force in such a way as to allow a practitioner to eject the mixture by hand.

Accordingly, as described herein by mixing an amount of an aqueous solution of Na-CMC with dry calcium sulphate (hemihydrate optionally comprising calcium sulphate dihydrate either as a powder or compacted particles) in ranges from about 0.1 mg-8 mg Na-CMC/g $CaSO_4$, such as e.g. 0.1 mg-6 mg Na-CMC/g $CaSO_4$, 0.1-4 mg Na-CMC/g $CaSO_4$, 0.1-3 mg Na-CMC/g $CaSO_4$, 0.1-2 mg Na-CMC/g $CaSO_4$, 0.1-1 mg Na-CMC/g $CaSO_4$, or 0.1-0.5 mg Na-CMC/g $CaSO_4$ or in $R_{opt}$ as described below, thereafter vigorously stirring with a spatula optionally and additionally treating the mixture with sonication in a water bath at a temperature of about 40° C. for less than 1 minute. If the resulting mixture fulfils the criteria as stated above the mixture is seen as ejectable when being able to be ejected through a 17 G cannula.

Furthermore, in the present context the term "ejectability time" is intended to mean the time during which the ready to use composition is ejectable through the orifice of e.g. a syringe optionally equipped with a cannula or needle or flexible tubing. By the compositions as mentioned above the ejecatbility time is from about 5 to about 15 min, or longer such as e.g. about 5 min to about 20 min, such as about 5 min to about 25 min, such as about 5 min to about 30 min, such as about 5 min to about 35 min, such as about 5 min to about 40 min, such as about 5 min to about 45 min, such as about 5 min to about 50 min or about 5 min to about 1 hour.

Dispersibility/Miscibility

In the present context, the term "dispersibility", "dispersability" or "miscibility" is intended to mean the ability of two or more components to be dispersible with one another to form a dispersion or suspension. In present invention, the calcium sulphate is usually in a powder form prior to mixing with the aqueous solution of Na-CMC. A high dispersibility results in a good mixing/contact between the two components with few or no lumps being formed in the final solution and thus represents no or low agglomeration. It is also intended to mean that after mixing of the aqueous solution of Na-CMC and calcium sulphate there is a very slow sedimentation of any particles and thus the resulting mix stays homogeneous from the point of mixing of the ingredients until the resulting mix is cured. In medical use when a mixture is administered through a syringe this is of importance as a high dispersibility will result in no caking at the bottom of the syringe resulting in clogging of the mix. Furthermore, one effect of high dispersability in this case is that the amount of water can be reduced while at the same time resulting in a manageable/ejectable homogeneous slurry.

Accordingly as described herein by mixing an amount of an aqueous solution of Na-CMC with dry calcium sulphate (hemihydrate optionally comprising calcium sulphate dihydrate either as a powder or compacted particles) in ranges from about 0.1 mg-8 mg Na-CMC/g $CaSO_4$, such as e.g. 0.1 mg-6 mg Na-CMC/g $CaSO_4$, 0.1-4 mg Na-CMC/g $CaSO_4$, 0.1-3 mg Na-CMC/g $CaSO_4$, 0.1-2 mg Na-CMC/g $CaSO_4$, 0.1-1 mg Na-CMC/g $CaSO_4$, or 0.1-0.5 mg Na-CMC/g $CaSO_4$ or in $R_{opt}$ as described below, thereafter vigorously stirring with a spatula optionally and additionally treating the mixture with sonication in a water bath at a temperature of about 40° C. for less than 1 minute. If no apparent sedimentation in the resulting mixture is visually seen, the mixture is considered to have a suitable dispersability according to the invention.

Curing and Solidification

In the present context, the term "solidification time, "setting time", "curing time" or "hardening time" is intended to mean the period in time from which the compositions according to the invention are initially formed until fully hydrated or cured. In the present context the solidification time is considered to be the time starting from the admixture of the ingredients of the composition until the said mixture forms a plastically non-deformable solid body.

Accordingly by admixing an aqueous solution of Na-CMC with dry calcium sulphate (hemihydrate optionally comprising calcium sulphate dihydrate either as a powder or compacted particles) in ranges from about 0.1 mg-8 mg Na-CMC/g $CaSO_4$, such as e.g. 0.1 mg-6 mg Na-CMC/g $CaSO_4$, 0.1-4 mg Na-CMC/g $CaSO_4$, 0.1-3 mg Na-CMC/g $CaSO_4$, 0.1-2 mg Na-CMC/g $CaSO_4$, 0.1-1 mg Na-CMC/g $CaSO_4$, or 0.1-0.5 mg Na-CMC/g $CaSO_4$ or in $R_{opt}$ as described below, thereafter vigorously stirring with a spatula optionally and additionally treating the mixture with sonication in a water bath at a temperature of about 40° C. for less than 1 minute, the time passes during the time span of ad-mixing the above ingredients until the resulting mix constitutes a solid plastically un-deformable body is considered as the solidification time.

Viscosity

By the term "viscosity" is intended to mean the dynamic or absolute viscosity (at 20° C. and normal pressure) which is a measure of the resistance of a fluid which is being deformed by either shear stress or extensional stress. "Viscosity" thus describes a fluid's internal resistance to flow and may be thought of as a measure of fluid friction. Consequently, the less viscous something is, the greater its ease of movement (fluidity). In the present context the relevant ranges of viscosity is from about 10-10.000 mPas, such as e.g. 20-9000 mPas, such as e.g. about 30-8000 mPas, such as e.g. about 40-7000 mPas, such as e.g. about 50-6000 mPas, such as e.g. about 70-5000 mPas, such as e.g. about 90-4000 mPas, such as e.g. about 100-3000 mPas or about 10 mPas, or about 20 mPas, or about 30 mPas, or about 40 mPas, or about 50 mPas or in range between the viscosity of pure deionised water and the viscosity of the particular batch/type of Na-CMC used, such as e.g. from about 1 mPas to about 20 mPas, such about 2 mPas, such as about 3 mPas, such as about 4 mPas, such as about 5 mPas such as about 6 mPas, such as about 7 mPas such as about 10 mPas, about 13 mPas, about 15 mPas about 20 mPas.

Consequently by ad-mixing an aqueous solution of Na-CMC with dry calcium sulphate (hemihydrate optionally comprising calcium sulphate dihydrate either as a powder or compacted particles) in ranges from about 0.1 mg-8 mg Na-CMC/g $CaSO_4$, such as e.g. 0.1 mg-6 mg Na-CMC/g $CaSO_4$, 0.1-4 mg Na-CMC/g $CaSO_4$, 0.1-3 mg Na-CMC/g $CaSO_4$, 0.1-2 mg Na-CMC/g $CaSO_4$, 0.1-1 mg Na-CMC/g $CaSO_4$, or 0.1-0.5 mg Na-CMC/g $CaSO_4$ or in $R_{opt}$ as described below, thereafter vigorously stirring with a spatula optionally and additionally treating the mixture with sonication in a water bath at a temperature of about 40° C. for less than 1 minute, a mixture of viscosity ranges such as about 10-10.000 mPas, such as e.g. 20-9000 mPas, such as e.g. about 30-8000 mPas, such as e.g. about 40-7000 mPas, such as e.g. about 50-6000 mPas, such as e.g. about 70-5000 mPas, such as e.g. about 90-4000 mPas, such as e.g. about 100-3000 mPas or about 10 mPas, or about 20 mPas, or about 30 mPas, or about 40 mPas, or about 50 mPas or in range between the viscosity of pure deionised water and the viscosity of the particular batch/type of Na-CMC used is achieved. In the present context, the term "bioresorbable" is intended to denote a material that can be dissolved and/or degraded in body fluids or organs or otherwise eliminated by the human body. It is envisaged that the implanted/injected compositions degrades from the point in time of administration to about 2-3 days, or to about 1 week, or to about 2 weeks, to about 3-weeks, to about 1 month, to about 3 months to about 6 months to about 1 year. The process>/progress of degradation can be monitored by standard techniques such as e.g. ultrasound, palpation, X-ray or MR techniques.

In the present context, the term "carboxymethylcellulose" is intended to encompass salts of carboxymethylcellulose including alkali or alkaline earth metal salts, notably such salts that are approved or can be approved for internal use in a mammal including a human. Sodium carboxymethylcellulose, also abbreviated herein as Na-CMC, has been found to be a suitable salt, but it is envisaged that other carboxymethylcellulose salts may have similar effects. Moreover, carboxymethylcelluloses can be obtained in various viscosity grades (low, medium, high). As it appears from the examples herein, the optimal ratio, $R_{opt}$, differs slightly depending on the viscosity grade employed. Relevant ranges of viscosity (the dynamic or absolute viscosity (at 20° C. and normal pressure)) of Na-CMC is from about 10-10.000 mPas, such as e.g. 20-9000 mPas, such as e.g. about 30-8000 mPas, such as e.g. about 40-7000 mPas, such as e.g. about 50-6000 mPas, such as e.g. about 70-5000 mPas, such as e.g. about 90-4000 mPas, such as e.g. about 100-3000 mPas or about 10 mPas, or about 20 mPas, or about 30 mPas, or about 40 mPas, or about 50 mPas, or in range from the viscosity of pure ionised water and the batch of Na-CM being used such as e.g. from about 1 mPas to about 20 mPas, such as about 2 mPas, such as about 3 mPas, such as about 4 mPas, such as about 5 mPas such as about 6 mPas, such as about 7 mPas such as about 10 mPas, about 13 mPas, about 15 mPas about 20 mPas.

The Optimal Ratio, $R_{opt}$, is from about 0.1 mg to about 15 mg, such as about 0.1 mg to about 10 mg, such as about 0.1 mg to about 7 mg, such as about 0.1 mg to about 5 mg, such as about 0.1 mg to about 3 mg, wherein $R_{opt}$ is defined as the ratio between the amount of carboxymethylcellulose (expressed as Na-CMC) in an aqueous solution and the total amount of calcium sulphate (hemihydrate optionally with calcium sulphate dihydrate) present in a ready-to-use composition.

In the present context, the narrow concentration window for the content of carboxymethylcellulose in a ready-to-use composition that allows for suitable properties with respect to ejectability, dispersability, viscosity and solidification is expressed as a ratio, R, between the amount of carboxymethylcellulose (expressed as Na-CMC) and the amount of calcium sulphate hemihydrate present in a ready-to-use composition.

In accordance with the above, the present invention provides a novel use of a carboxymethylcellulose, notably Na-CMC, to control solidification time of compositions comprising hydratable ceramics, notably calcium sulphate hemihydrate.

The present invention also provides for methods and compositions not involving surfactants (cationic, anionic or non-ionic) or detergent like compounds, such as ammonium salts, sulphonates, fatty acids and salts thereof, long chain alkyl amine salts, derivatives of acrylic acids, poloxamers such as pluronic and derivatives thereof etc. According to the present invention it is an undesirable/unwanted property to have bubble formation in the ready to use compositions and bubbles are known to be stabilised by the addition of detergent like compounds as mentioned above.

Moreover, the present invention provides a ready-to-use composition comprising a hydratable ceramic, notably calcium sulphate hemihydrate, and a carboxymethylcellulose, notably Na-CMC, wherein the weight ratio, R, between carboxymethylcellulose (notably Na-CMC) and the hydratable ceramic (notably calcium sulphate hemihydrate) is from about 0.1 mg carboxymethylcellulose (calculated as Na-CMC)/g calcium sulphate dihydrate to about 5 mg carboxymethylcellulose (calculated as Na-CMC)/g calcium sulphate dihydrate.

The ready-to-use composition is provided by mixing an aqueous medium containing the carboxymethylcellulose with a composition comprising or consisting of calcium sulphate hemihydrate, whereby a paste is formed that is in liquid form for 5-15 minutes and then solidifies. The aqueous medium is typically water and the content of carboxymethylcellulose is adjusted in such a way that the amount of carboxymethylcellulose in the final ready-to-use composition is within the limits claimed herein (i.e. the ratio between carboxymethylcellulose and calcium sulphate hemihydrate corresponds to from 0.1 mg Na-CMC/g calcium sulphate hemihydrate to 5 mg Na-CMC/g calcium sulphate hemihydrate), and the amount of water should at least correspond to the amount of water necessary to convert the calcium sulphate hemihydrate to calcium sulphate dihydrate.

Stoichiometrically, 1.000 g of $CaSO_4 \cdot \frac{1}{2}H_2O$ (0.007 mole) requires 0.186 g of water (1.5·0.007 mole) to be fully transformed to $CaSO_4 \cdot 2H_2O$, i.e. 1.186 g (0.007 mole). In order to obtain an acceptable consistency of the resulting paste, the amount of water per gram of calcium sulphate hemihydrate should not exceed 1.0 g, i.e. 1.0 ml. A suitable concentration range of Na-CMC in water is 0.05-1.0% w/w, more preferably 0.2-0.4% w/w. The actual concentration of Na-CMC depends on the specific composition of the calcium sulphate powder mixture, as well as on the molecular weight of Na-CMC being used.

According to the invention, the one or more bioresorbable hydratable ceramics may be chosen from several bioresorbable and biocompatible hydratable ceramics, the ceramic may be non-hydrated or semi-hydrated or partly hydrated. Suitable hydratable ceramics for use in a composition according to the invention may be selected from the group consisting of calcium sulphate such as, e.g., α-calcium sulphate, β-calcium sulphate; calcium sulphate hemihydrate; calcium sulphate dihydrate (i.e. in semi-hydrated or partly hydrated form), or any combination thereof.

In a preferred embodiment of the invention the one or more bioresorbable and hydratable ceramics is calcium sulphate hemihydrate.

Calcium sulphate hemihydrate is preferably in the form of a powder, e.g. with a mean particle size at the most about 75 μm such as, e.g., at the most about 50 μm, at the most about 25 μm or at the most about 10 μm. Alternatively the powder may be composed of two (or more) grain size fractions; e.g. one <10 μm of grains and one with a mean particle size of at the most about 75 μm such as, e.g., at the most about 50 μm, at the most about 25 μm or at the most about 10 μm.

However, in a preferred embodiment, the calcium sulphate part of the composition may in addition to the above-mentioned one or more calcium sulphate hemihydrate grains contain non-compressed and/or compressed particles of calcium sulphate dihydrate. A composition may thus comprise one part of compressed and/or non-compressed calcium sulphate dihydrate particles and one part calcium sulphate hemihydrate. Alternatively, the composition may comprise one part of compressed calcium sulphate dihydrate particles and at least two parts calcium sulphate hemihydrate, such as e.g. three parts, four parts, or five parts of calcium sulphate hemihydrate.

The presence of non-compressed and/or compressed particles of calcium sulphate dihydrate in the calcium sulphate hemihydrate composition leads to a triggering (acceleration) of the solidification process, as calcium sulphate dihydrate crystals acts as nucleation sites for the transformation of hemihydrate to dihydrate. Thus, the presence of calcium sulphate dihydrate in the starting composition imposes an even shorter solidification time.

Compressed particles of calcium sulphate dihydrate may be obtained by subjecting calcium sulphate hemihydrate to an externally applied pressure during the hydration process. The external pressure is applied with any suitable method, e.g. with mechanical or hydraulic means. The principle of obtaining very dens ceramics by hydration under pressure may be applied to any hydratable ceramic. This method does not require an elevated temperature to obtain a dense structure, as in normal sintering processes.

Alternatively the particles may be in the form of highly densified ceramic particles, as described in the international publication WO 2007/104549, whereby calcium sulphate hemihydrate has been subjected to an externally applied pressure, e.g. a compression, in combination with hydration under external pressure. By this method the densification is carried out at the same time as the hydration of the ceramic takes place in order to obtain a highly densified structure. Compressed particles of calcium sulphate dihydrate are produced by an externally applied pressure, e.g. a compression, optionally in combination with an at least partly hydration under external pressure, whereby the pore size and the porosity of the at least partly hydrated ceramic are decreased leading to a highly densified structure of the particles. Accordingly, densification/compression is carried out at the same time as the hydration of the calcium sulphate hemihydrate takes place in order to obtain a highly densified structure. The highly densified structure obtained (exemplified with calcium sulphate) is characterized by a typical pore size of at the most about 100 nm such as, e.g., at the most about 75 nm, at the most about 50 nm or at the most about 10 nm; and a porosity of at the most about 10% such as, e.g., at the most about 5%, at the most about 3%, at the most about 2% or at the most about 1%. For example, a hydration under applied pressure of at least 100 MPa, and preferably of 200 MPa or more, reduces the porosity to below 10% and reduces the pore size to below 100 nm.

Accordingly, several techniques may be used to apply the external pressure, for example uniaxial pressing or isostatic pressing (hot or cold). Cold Isostatic Pressing (CIP), applied to preformed bodies of calcium sulphate containing the selected active components, has been found to be an effective method to produce highly densified and homogenous bodies. For an optimal densification, the calcium sulphate bodies may be covered with e.g. a capsule (e.g. an elastic balloon) during pressurising. Normally, the applied pressure should be at least 50 MPa such as, e.g., at least 100 MPa, at least about 200 MPa, preferably 300 MPa or above. However, the pressure required is dependent on the pressing apparatus employed. Thus, the above-mentioned pressures are suitable for use in case of CIP, whereas in the case of e.g. a uniform uniaxial pressing, pressures are normally applied that are higher such as, e.g., at the most about 200 MPa, preferably about 300 MPa or more, about 400 MPa or more, or about 500 MPa or more. The method is described in detail in WO 2007/104549, which is incorporated herein by reference.

Compressed particles of calcium sulphate dihydrate may have a particle size of from about 50-600 μm, such as e.g. from about 100-500, from about 100-400, or from about 125-300 μm. It is further envisaged that the composition may comprise one or more size fractions of compressed calcium sulphate dihydrate particles.

Both the calcium sulphate hemihydrate powder, the calcium sulphate dihydrate powder as well as the compressed particles of calcium sulphate dihydrate or the aqueous solution of Na-CMC may comprise one or more therapeutically, prophylactically and/or diagnostically active substances. The active substances may comprise, but are not limited to, androgens or derivates thereof (e.g. testosterone), antiandrogens (cyproteron, flutamide, 2-hydroxyflutamide, bicalutamide, nilutamide) or derivatives thereof, oestrogens or derivates thereof, anti-oestrogens (e.g. tamoxifen, toremifen) or derivates thereof, gestagens or derivatives thereof, antigestagens or derivates thereof, oligonucleotides, progestagens or derivates thereof, gonadotropin-releasing hormone or analogues or derivates thereof, gonadotropin inhibitors or derivates thereof, adrenal and prostate enzyme synthesis inhibitors (such as α-reductase inhibitors), membrane efflux and membrane transport proteins (such as PSC 833, verapamil), and other cytostatic agents, immune system modulators and angiogenesis inhibitors alone or in combinations.

Preferably, the active substances are selected from flutamide, 2-hydroxyflutamide and/or bicalutamide, including any combinations thereof, and any other antiandrogen.

The drug load in the composition, i.e. the amount of active substance in the composition, can vary within wide limits. The active substance can be present in the aqueous solution which is added to the calcium sulphate or in the compacted or non-compacted/powders of the calcium sulphate being either the hemihydrate or dihydrate. The concentration of the active substance in the ready-to-use composition according to the invention may be in the range from about 0.01% w/w to about 75% w/w such as, e.g. from about 0.01% w/w to about 50% w/w, from about 0.01% w/w to about 40% w/w from about 0.05% w/w to about 30% w/w, from about 0.05% w/w to about 20% w/w or from about 0.1% w/w to about 10% w/w. Some active substances may thus suitably be present in an amount of up to about 75% w/w in the calcium sulphate hemihydrate powder and/or the calcium sulphate dihydrate particles or aqueous solution, whereas the active substance may also, depending on the nature and strength of the active substance in question, be present in the composition in much smaller amounts.

By mixing calcium sulphate hemihydrate and/or compressed particles of calcium sulphate dihydrate with Na-CMC a paste is formed which preferably have prolonged solidification time, suitable ejectability and good dispersability.

Na-CMC is an anionic, water-soluble polymer derived from cellulose reacted with sodium monochloroacetate. The polymer is characterized by its molecular weight, which affects the viscosity when dissolved in water, and the degree of substitution, which affects the thixotropic and adsorbing properties of the resulting solution. The degree of substitution, or DS, is an average measure of the number of sodium carboxymethyl groups ($-CH_2-COONa$) bound to the hydroxyl groups of the anhydroglucose units that make up the cellulose backbone. Na-CMC is soluble in cold and hot water at a pH above about 4. Na-CMC may be purchased from several commercial manufactures including the non-limiting examples of C9481 from Sigma-Aldrich, and Blanose 7LF PH, Blanose 7M1F PH, Blanose 7MF PH, Blanose 7M8SF, Blanose 9M31F, Blanose 9M31CF, Blanose 9M31XF PH, Blanose 7M31C, Blanose 7HF, and Blanose 7H4F, all from Hercules.

The inventors have found that by adding an aqueous solution of Na-CMC to the above calcium sulphate composition comprising hemihydrate with or without compressed and/or non-compressed dihydrate particles it is possible to adjust the solidification time of the so formed paste by small adjustments in the Na-CMC concentration, while at the same time retain an acceptable miscibility of the formed paste, as well as an acceptable ejectability through a syringe with a small cannula.

Furthermore, the inventors have surprisingly found that by addition of Na-CMC by the ratios defined herein, the paste to be ejected remains reproduceably (reliably) ejectable throughout the entire ejection procedure 5-15 min which is especially important towards the end of the ejection procedure. Other compositions not employing Na-CMC will be more sensitive to the solidification taking place towards the end of the injection procedure which will results in an unreliable administration further resulting in an uncertainty in the exact dose of the pharmaceutical active ingredient as only a part of the complete compositions has been administered. Present inventors have found that by addition of Na-CMC, this difficulty is circumvented and thus allows for more safe administration/injection of the entire prepared composition and thus a reliable, robust composition is provided for allowing exact dosing of the pharmaceutically active ingredient(s).

Consequently, by using Na-CMC in compositions according to present invention the solidification time, viscosity and dispersability can be fine tuned to fit the specific application of the composition. As previously mentioned, one important object of the invention is to reduce the mixing amount of water in the ready-to-use composition as this will influence the final volume of the composition to be injected. For some applications it is desirable to have a low volume in the composition to be injected as this will reduce the stress on the organ into which the composition is injected. However, without the use of a dispersing agent (such as e.g. Na-CMC) the solidification time will become too short for the purpose of the invention and the resulting composition will contain parts that are of a very heterogeneous structure.

Na-CMC-based solutions thus contributes with the combined effects of prolonged solidification rate, increased viscosity and improved dispersability of the powder in the solution. All these effects are achieved with Na-CMC as the only additive to the formulation. These effects are particularly beneficial to formulations based on powders being mixtures of both calcium sulphate hemihydrates and di-hydrate. The di-hydrate accelerates the hydration (solidification), i.e. the transformation of the hemi-hydrate to di-hydrate.

Importantly, the Na-CMC needs to be completely dissolved in an aqueous solution to obtain this effect. One way of obtaining complete dissolution of Na-CMC is by mixing the dry polymer powder with water (e.g. fresh membrane-filtered water such as Milli-Q water). This mixture is then stirred for a few hours at room temperature and next put in a refrigerator overnight to completely dissolve the polymer material (whereby any lumps formed during mixing are dissolved during standing). Another way is to provide the Na-CMC in dry form, preferably with a large surface area, so that the polymer swells and dissolves instantaneously and completely in situ. Examples of preferable dry forms are thin films and freeze-dried fine powders As discussed above, the amount of Na-CMC added to the pharmaceutical composition of the invention is given by weight in mg of Na-CMC to the calcium sulphate hemihydrate ($CaSO_4.\frac{1}{2}H_2O$) component of the composition in grams. The amount of Na-CMC in a ready-to-use composition comprising calcium sulphate hemihydrate is from about 0.1 mg-8 mg Na-CMC/g $CaSO_4$ hemihydrate, such as e.g. 0.1 mg-6 mg Na-CMC/g $CaSO_4$ hemihydrate, 0.1-4 mg Na-CMC/g $CaSO_4$ hemihydrate, 0.1-3 mg Na-CMC/g $CaSO_4$ hemihydrate, 0.1-2 mg Na-CMC/g $CaSO_4$ hemihydrate, 0.1-1 mg Na-CMC/g $CaSO_4$ hemihydrate, or 0.1-0.5 mg Na-CMC/g $CaSO_4$ hemihydrate.

If calcium sulphate dihydrate also is present in the composition a relevant parameter may also be the ratio between the weight in mg of Na-CMC to the total weight in gram of calcium sulphate, i.e. the calcium sulphate component includes the weight of calcium sulphate as hemihydrate and dihydrate in grams. Thus, the amount of Na-CMC is given as mg Na-CMC/g $CaSO_4$, wherein $CaSO_4$=grams of $CaSO_4.\frac{1}{2}H_2O$ (e.g. as powder)+grams of $CaSO_4.2H_2O$ (e.g. as compressed particles). However, a preferred ratio is the one relative to calcium sulphate hemihydrate as this is the component that takes up water. In some of the tables herein, the other ratio has also been calculated as suitable ratios seems to be the following: The amount of Na-CMC in a ready-to-use composition comprising calcium sulphate hemihydrate and another calcium sulphate, notably calcium sulphate dihydrate is from about 0.1 mg-8 mg Na-CMC/g $CaSO_4$, such as e.g. 0.1 mg-6 mg Na-CMC/g $CaSO_4$, 0.1-4 mg Na-CMC/g $CaSO_4$, 0.1-3 mg Na-CMC/g $CaSO_4$, 0.1-2 mg Na-CMC/g $CaSO_4$, 0.1-1 mg Na-CMC/g $CaSO_4$, or 0.1-0.5 mg Na-CMC/g $CaSO_4$, wherein $CaSO_4$ is the total weight of calcium sulphate (i.e. sum of the weight of all calcium sulphates in the composition), wherein $CaSO_4$ denotes the total amount of calcium sulphate, i.e. the sum of calcium sulphate hemihydrate and calcium sulphate dihydrate Further embodiments of the composition are the following, wherein the weight ratio of Na-CMC and calcium sulphate hemihydrate ranges from 0.25 mg/g to 0.75 mg/g and the weight ratio of Na-CMC and total calcium sulphate content ranges from 0.2 mg/g to 0.5 mg/g. Also embodiments with equal amounts of $CaSO_4.2H_2O$ and $CaSO_4.\frac{1}{2}H_2O$ are of relevance to the invention.

| Na-CMC (mg)/Calcium sulphate dihydrate(g) | Embodiment 1[1] | Embodiment 2[1] | Embodiment 3[1] |
|---|---|---|---|
| 5.5 | 1 part $CaSO_4 \cdot 2H_2O$[2], 2 parts $CaSO_4 \cdot \frac{1}{2}H_2O$, and 0.0055 part Na-CMC (aq.)[3] R = 2.8 | 1 part $CaSO_4 \cdot 2H_2O$[2], 3 parts $CaSO_4 \cdot \frac{1}{2}H_2O$, and 0.0055 part Na-CMC (aq.)[3] R = 1.8 | 1 part $CaSO_4 \cdot 2H_2O$[2], 4 parts $CaSO_4 \cdot \frac{1}{2}H_2O$, and 0.0055 part Na-CMC (aq.)[3] R = 1.4 |
| 4.5 | 1 part $CaSO_4 \cdot 2H_2O$[2], 2 parts $CaSO_4 \cdot \frac{1}{2}H_2O$, and 0.0045 part Na-CMC (aq.)[3] R = 2.3 | 1 part $CaSO_4 \cdot 2H_2O$[2], 3 parts $CaSO_4 \cdot \frac{1}{2}H_2O$, and 0.0045 part Na-CMC (aq.)[3] R = 1.5 | 1 part $CaSO_4 \cdot 2H_2O$[2], 4 parts $CaSO_4 \cdot \frac{1}{2}H_2O$, and 0.0045 part Na-CMC (aq.)[3] R = 1.2 |
| 4.0 | 1 part $CaSO_4 \cdot 2H_2O$[2], 2 parts $CaSO_4 \cdot \frac{1}{2}H_2O$, and 0.004 part Na-CMC (aq.)[3] R = 2 | 1 part $CaSO_4 \cdot 2H_2O$[2], 3 parts $CaSO_4 \cdot \frac{1}{2}H_2O$, and 0.004 part Na-CMC (aq.)[3] R = 1.3 | 1 part $CaSO_4 \cdot 2H_2O$[2], 4 parts $CaSO_4 \cdot \frac{1}{2}H_2O$, and 0.004 part Na-CMC (aq.)[3] R = 1 |
| 3.5 | 1 part $CaSO_4 \cdot 2H_2O$[2], 2 parts $CaSO_4 \cdot \frac{1}{2}H_2O$, and 0.0035 part Na-CMC (aq.)[3] R = 1.8 | 1 part $CaSO_4 \cdot 2H_2O$[2], 3 parts $CaSO_4 \cdot \frac{1}{2}H_2O$, and 0.0035 part Na-CMC (aq.)[3] R = 1.2 | 1 part $CaSO_4 \cdot 2H_2O$[2], 4 parts $CaSO_4 \cdot \frac{1}{2}H_2O$, and 0.0035 part Na-CMC (aq.)[3] R = 0.9 |
| 3.0 | 1 part $CaSO_4 \cdot 2H_2O$[2], 2 parts $CaSO_4 \cdot \frac{1}{2}H_2O$, and 0.003 part Na-CMC (aq.)[3] R = 1.5 | 1 part $CaSO_4 \cdot 2H_2O$[2], 3 parts $CaSO_4 \cdot \frac{1}{2}H_2O$, and 0.003 part Na-CMC (aq.)[3] R = .1 | 1 part $CaSO_4 \cdot 2H_2O$[2], 4 parts $CaSO_4 \cdot \frac{1}{2}H_2O$, and 0.003 part Na-CMC (aq.)[3] R = 0.8 |

-continued

| Na-CMC (mg)/Calcium sulphate dihydrate(g) | Embodiment 1[1] | Embodiment 2[1] | Embodiment 3[1] |
|---|---|---|---|
| 2.5 | 1 part $CaSO_4 \cdot 2H_2O$[2], 2 parts $CaSO_4 \cdot \frac{1}{2}H_2O$, and 0.0025 part Na-CMC (aq.)[3] R = 1.3 | 1 part $CaSO_4 \cdot 2H_2O$[2], 3 parts $CaSO_4 \cdot \frac{1}{2}H_2O$, and 0.0025 part Na-CMC (aq.)[3] R = 0.83 | 1 part $CaSO_4 \cdot 2H_2O$[2], 4 parts $CaSO_4 \cdot \frac{1}{2}H_2O$, and 0.0025 part Na-CMC (aq.)[3] R = 0.63 |
| 2.0 | 1 part $CaSO_4 \cdot 2H_2O$[2], 2 parts $CaSO_4 \cdot \frac{1}{2}H_2O$, and 0.002 part Na-CMC (aq.)[3] R = 1 | 1 part $CaSO_4 \cdot 2H_2O$[2], 3 parts $CaSO_4 \cdot \frac{1}{2}H_2O$, and 0.002 part Na-CMC (aq.)[3] R = 0.67 | 1 part $CaSO_4 \cdot 2H_2O$[2], 4 parts $CaSO_4 \cdot \frac{1}{2}H_2O$, and 0.002 part Na-CMC (aq.)[3] R = 0.5 |
| 1.5 | 1 part $CaSO_4 \cdot 2H_2O$[2], 2 parts $CaSO_4 \cdot \frac{1}{2}H_2O$, and 0.0015 part Na-CMC (aq.)[3] R = 0.75 | 1 part $CaSO_4 \cdot 2H_2O$[2], 3 parts $CaSO_4 \cdot \frac{1}{2}H_2O$, and 0.0015 part Na-CMC (aq.)[3] R = 0.5 | 1 part $CaSO_4 \cdot 2H_2O$[2], 4 parts $CaSO_4 \cdot \frac{1}{2}H_2O$, and 0.0015 part Na-CMC (aq.)[3] R = 0.38 |
| 1 | 1 part $CaSO_4 \cdot 2H_2O$[2], 2 parts $CaSO_4 \cdot \frac{1}{2}H_2O$, and 0.001 part Na-CMC (aq.)[3] R = 0.5 | 1 part $CaSO_4 \cdot 2H_2O$[2], 3 parts $CaSO_4 \cdot \frac{1}{2}H_2O$, and 0.001 part Na-CMC (aq.)[3] R = 0.33 | 1 part $CaSO_4 \cdot 2H_2O$[2], 4 parts $CaSO_4 \cdot \frac{1}{2}H_2O$, and 0.001 part Na-CMC (aq.)[3] R = 0.25 |
| 0.95 | 1 part $CaSO_4 \cdot 2H_2O$[2], 2 parts $CaSO_4 \cdot \frac{1}{2}H_2O$, and 0.00095 part Na-CMC (aq.)[3] R = 0.48 | 1 part $CaSO_4 \cdot 2H_2O$[2], 3 parts $CaSO_4 \cdot \frac{1}{2}H_2O$, and 0.00095 part Na-CMC (aq.)[3] R = 0.32 | 1 part $CaSO_4 \cdot 2H_2O$[2], 4 parts $CaSO_4 \cdot \frac{1}{2}H_2O$, and 0.00095 part Na-CMC (aq.)[3] R = 0.24 |
| 0.85 | 1 part $CaSO_4 \cdot 2H_2O$[2], 2 parts $CaSO_4 \cdot \frac{1}{2}H_2O$, and 0.00085 part Na-CMC (aq.)[3] R = 0.43 | 1 part $CaSO_4 \cdot 2H_2O$[2], 3 parts $CaSO_4 \cdot \frac{1}{2}H_2O$, and 0.00085 part Na-CMC (aq.)[3] R = 0.28 | 1 part $CaSO_4 \cdot 2H_2O$[2], 4 parts $CaSO_4 \cdot \frac{1}{2}H_2O$, and 0.00085 part Na-CMC (aq.)[3] R = 0.21 |
| 0.75 | 1 part $CaSO_4 \cdot 2H_2O$[2], 2 parts $CaSO_4 \cdot \frac{1}{2}H_2O$, and 0.00075 part Na-CMC (aq.)[3] R = 0.38 | 1 part $CaSO_4 \cdot 2H_2O$[2], 3 parts $CaSO_4 \cdot \frac{1}{2}H_2O$, and 0.00075 part Na-CMC (aq.)[3] R = 0.25 | 1 part $CaSO_4 \cdot 2H_2O$[2], 4 parts $CaSO_4 \cdot \frac{1}{2}H_2O$, and 0.00075 part Na-CMC (aq.)[3] R = 0.19 |
| 0.65 | 1 part $CaSO_4 \cdot 2H_2O$[2], 2 parts $CaSO_4 \cdot \frac{1}{2}H_2O$, and 0.00065 part Na-CMC (aq.)[3] R = 0.33 | 1 part $CaSO_4 \cdot 2H_2O$[2], 3 parts $CaSO_4 \cdot \frac{1}{2}H_2O$, and 0.00065 part Na-CMC (aq.)[3] R = 0.22 | 1 part $CaSO_4 \cdot 2H_2O$[2], 4 parts $CaSO_4 \cdot \frac{1}{2}H_2O$, and 0.00065 part Na-CMC (aq.)[3] R = 0.17 |

[1]all parts are in "parts per weight"
[2]$CaSO_4 \cdot \frac{1}{2}H_2O$ = calcium sulphate hemihydrate; $CaSO_4 \cdot 2H_2O$ = calcium sulphate dihydrate particles
[3]Na-CMC (dissolved in an aqueous medium) given as parts of Na-CMC
R = mg Na-CMC/g $CaSO_4 \cdot \frac{1}{2}H_2O$ Each of the above embodiments may additionally contain an active substance such as e.g. flutamide, 2-hydroxyflutamide and/or bicalutamide, including any combinations thereof. The concentration of the active substance is generally in a range from about 0.01% w/w to about 75% w/w of calcium sulphate hemihydrate powder and/or calcium sulphate dihydrate particles such as, e.g. from about 0.01% w/w to about 50% w/w, from about 0.01% w/w to about 40% w/w from about 0.05% w/w to about 30% w/w, from about 0.05% w/w to about 20% w/w or from about 0.1% w/w to about 10% w/w.

Specific ready-to-use compositions of the invention comprise 1 part (e.g. 0.33 g) $CaSO_4.2H_2O$ with an active substance,
1 part (e.g. 0.33 g) $CaSO_4.\frac{1}{2}H_2O$ with an active substance,
1 part (e.g. 0.33 g) $CaSO_4.\frac{1}{2}H_2O$ without an active substance, and from about 0.0015-0.0027, preferably 0.0022-0.0025, parts of Na-CMC, notably Blanose 9M31XF (aq.) (e.g. 0.6-0.9, preferably 0.7-0.8, g of a 0.30% aqueous solution). Alternatively, e.g. 0.7-1.0, preferably 0.8-0.9, g of a 0.25% aqueous solution can be used.

A ready-to-use composition according to the present invention has a good miscibility and can be ejected from a syringe for about 10-15 minutes or more through a 15-17 G or smaller cannula.

Other ready-to-use compositions may comprise 2 parts (e.g. 0.50 g) $CaSO_4.2H_2O$ with an active substance,
1 part (e.g. 0.25 g) $CaSO_4.\frac{1}{2}H_2O$ with an active substance,
1 part (e.g. 0.25 g) $CaSO_4.\frac{1}{2}H_2O$ without an active substance, and from about 0.0015-0.0027, preferably 0.0018-0.0023, parts of Na-CMC, notably Blanose 9M31XF (aq.) (e.g. 0.6-0.8, preferably 0.6-0.7, g of a 0.30% aqueous solution).

Each of the above compositions may additionally contain an active substance such as e.g. flutamide, 2-hydroxyflutamide and/or bicalutamide, including any combinations thereof, in the range from about 0.01% w/w to about 75% w/w of calcium sulphate hemihydrate powder and/or calcium sulphate dihydrate particles such as, e.g. from about 0.01% w/w to about 50% w/w, from about 0.01% w/w to about 40% w/w from about 0.05% w/w to about 30% w/w, from about 0.05% w/w to about 20% w/w or from about 0.1% w/w to about 10% w/w.

A paste obtained (e.g. the ready-to-use composition) has a good miscibility in the syringe, and will be ejectable for about 10-15 minutes or more through a 15-17 G or larger cannula such as e.g. 6 G, 8 G, 9 G, 10 G, 11 G 12 G, 13 G, 14 G, 16 G Alternatively smaller cannula can be used such as 18 G or 19 G or 20 G or smaller cannula sizes such as 21 G, 22 G, 23 G, 24 G, or 26 G.

In the present invention a kit is also contemplated to be used in the treatment method, compositions and use according to the invention with the respective ranges, amounts or ratios of all components as disclosed herein.

The kit may comprise
i) a first component comprising
(a) calcium sulphate ($CaSO_4$) hemihydrate,
(b) optionally calcium sulphate dihydrate in a solid or semi solid form, and
ii) a second component comprising
(c) a carboxymethylcellulose, notably sodium carboxymethylcellulose (Na-CMC), wherein the ratio R of carboxymethylcellulose to calcium sulphate in the kit is from about 0.1 mg carboxymethylcellulose (calculated as Na-CMC)/g calcium sulphate to about 8 mg carboxymethylcellulose (calculated as Na-CMC)/g calcium sulphate.

The ratio is from about 0.5 mg carboxymethylcellulose (calculated as Na-CMC)/g calcium sulphate to about 3 mg carboxymethylcellulose (calculated as Na-CMC)/g calcium sulphate or the ratio R is from about 1 mg carboxymethylcellulose (calculated as Na-CMC)/g calcium sulphate to about 3 mg carboxymethylcellulose (calculated as Na-CMC)/g calcium sulphate.

It is furthermore contemplated that the second component further comprises an aqueous medium including water and wherein the carboxymethylcellulose in the second component is dissolved in water wherein concentration of carboxymethylcellulose in water is from about 0.05% w/w to about 1% w/w.

The kit may also comprising an active substance in component i) and/or component ii), wherein the active substance is an antiandrogen or derivatives thereof such as e.g. cyproteron, flutamide, 2-hydroxyflutamide or the like.

The kit may also comprise calcium sulphate dihydrate present in component ii) in compressed form or particles as discussed herein and wherein said particles may further comprise an active substance. The kit wherein the calcium sulphate hemihydrate of component i) is present in admixture with an active substance. Optionally the kit does not contain acetic acid in component ii).

The composition of the invention can be used for local or systemic treatment in various diseases including, but not limited to, e.g., pain, neurological diseases (Alzheimer, Parkinson), autoimmune diseases, immunological diseases, and diseases responding to immunological and immunomodulating therapy (hepatitis, MS, tumours), infections, inflammations, metabolic diseases, obesitas, diseases in the uro-genital tract, cardiovascular diseases (including blood pressure), hematopoietic, anticoagulant, thrombolytic and antiplatelet diseases, chemotherapy of parasitic infections, microbial diseases and neoplastic diseases, hypercholesterolemia, dyslipidemia, hematopoetic diseases, respiratory diseases (asthma, chronical lung obstruction), diseases of the kidney, gastrointestinal diseases, liver diseases, hormonal disruption, replacement and substitution, vitamin replacement and substitution. However a specific embodiment of the invention is the treatment of prostate-related diseases such as e.g. prostate cancer, benign prostatic hyperplasia or acute and chronic prostatitis.

Thus, an embodiment the invention relates to method for treating the above-mentioned diseases, and especially prostate related diseases, such as e.g. prostate cancer, benign prostatic hyperplasia or acute and chronic prostatitis, by use of composition of the invention. Another aspect of the invention relates to the use of said composition for the preparation of a medicament for the treatment of the above-mentioned diseases, and especially prostate related diseases, such as e.g. prostate cancer, benign prostatic hyperplasia or acute and chronic prostatitis.

It is thus envisaged that the compositions according to present invention can be administered by injection to tissue for local treatment of the above mentioned diseases/conditions. The injection may be e.g. parenteral, intradermal, subcutaneous, intramuscular, intravenous, intraosseous, and intraperitoneal or direct injection into a specific organ/tissue, e.g. prostate. Other methods of administration are e.g. intrathecally, inttraarterially, intracranially, intraocular, oral rectal and vaginal.

To further illustrate the invention, the following examples are provided. The examples are not to be construed as limiting.

Abbreviations used herein are as follows:
Na-CMC sodium carboxymethylcellulose
2-HOF 2-Hydroxyflutamide
MC Methylcellulose
HAc Acetic acid

EXAMPLES

Example 1

Materials and Methods

In Table 1 is given a summary of all Na-CMC samples used in the examples given herein. The samples were either purchased from Sigma-Aldrich (Sample No. 1), Apoteket AB (one sample of Blanose®, Sample No. 8) or kindly provided by Hercules Inc. via Bröste AB (nine samples of Blanose®). In all, ten samples of Blanose were used; the samples designated 'PH' in Table 1 are compliant with the monograph requirements of Ph. Eur. and USP/NF. Among the samples provided by Bröste, four samples were used in the examples given herein.

TABLE 1

Data on the various Na-CMC samples used in the examples. Data on viscosity and degree of substitution are taken from the Certificates of Analysis.

| No. | Manufacturer | Type | Product name | Batch number | Viscosity[1] (mPas) | Degree of substitution[2] |
|---|---|---|---|---|---|---|
| 1 | Sigma-Aldrich | Medium viscosity | C9481[3] | 065K0174 | Nominal: 400-800 mPas [2%] | NA |

TABLE 1-continued

Data on the various Na-CMC samples used in the examples. Data on viscosity and degree of substitution are taken from the Certificates of Analysis.

| No. | Manufacturer | Type | Product name | Batch number | Viscosity[1] (mPas) | Degree of substitution[2] |
|---|---|---|---|---|---|---|
| 2 | Hercules | Low viscosity | Blanose 7LF PH | 71044 | 42 [2%; 1; 60 rpm] | 0.78 |
| 3 | Hercules | Medium viscosity | Blanose 7M1F PH | 72329 | 53 [2%; 1; 60 rpm] | 0.81 |
| 4 | Hercules | Medium viscosity | Blanose 7MF PH | 71042 | 468 [2%; 2; 30 rpm] | 0.86 |
| 5 | Hercules | Medium viscosity | Blanose 7M8SF | 70425 | 508 [2%; 2; 30 rpm] | 0.91 |
| 6 | Hercules | Medium viscosity | Blanose 9M31F | 70142 | 1680 [2%; 3; 30 rpm] | 0.95 |
| 7 | Hercules | Medium viscosity | Blanose 9M31CF | 71261 | 2170 [2%; 3; 30 rpm] | 0.73 |
| 8 | Hercules (via Apoteket) | Medium viscosity | Blanose 9M31XF PH | 60472 | 2620 [2%; 3; 30 rpm] | 0.92 |
| 9 | Hercules | Medium viscosity | Blanose 7M31C | 62667 | NA | 0.70 |
| 10 | Hercules | High viscosity | Blanose 7HF | 71241 | 1780 [1%; 3; 30 rpm] | 0.72 |
| 11 | Hercules | High viscosity | Blanose 7H4F | 92344 | 5940 [1%; 3; 30 rpm] | 0.85 |

[1] Viscosity (1 mPas = 1 cP) of an aqueous solution measured using the indicated parameters [concentration in percent by weight; Brookfield spindle number; and settings in rpm].
[2] Average number of carboxymethyl groups per anhydroglucose unit of the cellulose backbone.
[3] Meets USP testing specifications according to the manufacturer.
NA = Data not available.

Of particular importance in the present invention is that the Na-CMC used is in an aqueous solution. Aqueous solutions of Na-CMC were prepared by mixing the dry polymer powder with fresh membrane-filtered water (Milli-Q water). The mixtures were stirred for a few hours at room temperature and then put in a refrigerator overnight to completely dissolve the polymer material (any lumps formed during mixing were dissolved by this). The resulting clear, more or less viscous solutions were kept in the refrigerator until use, normally within a week. All concentrations given in the examples herein are by percent by weight (w/w).

According to the specifications from Hercules, aqueous solutions of Na-CMC have a pH in the range of 6.5 to 8.0. In the examples given, pH was not adjusted.

As a control to Na-CMC, a mixture of 1.0% methylcellulose (MC) and 1.0% acetic acid (HAc) in water was used, prepared by Apoteket AB.

Various batches of calcium sulphate hemihydrate ($CaSO_4 \cdot \frac{1}{2}H_2O$), both a commercially available batch from Sigma-Aldrich (Cat. No. 30,766-1, lot 06106JD-046) and batches prepared in-house by LIDDS (denoted CRVM), were used. The latter were based on calcium sulphate dihydrate ($CaSO_4 \cdot 2H_2O$) from Carl Roth GmbH, Germany, which was heated at 200° C. for 4 h in air.

Also, various batches of compressed particles, comprising $CaSO_4 \cdot 2H_2O$ and 2-hydroxyflutamide (2-HOF), were used in the test. The compacted granules were manufactured by isostatic compression. To produce the compacted granules, an amount of 10 g of dry calcium sulphate hemihydrate/2-HOF powder was used for each bar. The powder was poured into a two-sided mono-axial stainless steel compression die. A punch fitting to the die was placed on top of the manually distributed powder bed. By applying a pressure of approximately 2 tons with an axial mechanical press the powder was pre-compacted into dry bars. On each of the four long edges of the bar a certain amount of sterilised water was dropped and permeation was awaited. The moistened bar was covered by a condom which was sealed by knotting, trying to trap as little air as possible. The hence sealed bar was placed in the sample cage of a cold isostatic press and a pressure of 4000 bar was applied for 60 minutes. After the isostatic compression, the bars were grinded and milled to a grains size of 125 to 500 micrometers.

One batch of commercially available $CaSO_4 \cdot 2H_2O$ was used in Example 3 (Compactrol; batch 06021C).

In Example 2 and 3 samples with $CaSO_4 \cdot \frac{1}{2}H_2O$ only were tested, followed by examples wherein samples with compressed particles containing 2-HOF plus $CaSO_4 \cdot \frac{1}{2}H_2O$ were used, whereas samples with 2-HOF both in the compressed particles (for extended release) and in the matrix (for immediate release or 'booster') were used in Examples 6-8.

Normally, from about 0.1 mg-8 mg Na-CMC/g $CaSO_4$ (i.e. the total amount of calcium sulphate by weight (including both hemihydrate and dihydrate) to which Na-CMC is added) was mixed to form a paste. The calcium part of the composition could of different ratios of calcium sulphate hemihydrate and dihydrate, e.g. one part of compressed particles of $CaSO_4 \cdot 2H_2O$ and two parts of $CaSO_4 \cdot \frac{1}{2}H_2O$ as further exemplified in e.g. Example 8.

To evaluate the properties of the formed paste both plastic cups (using a spatula for stirring), and devices based on plastic syringes, either normal or modified in different ways were used.

At the time of mixing of the powder mix of calcium sulphate hemihydrate and/or dihydrate particles and Na-CMC solution a stopwatch was started. A paste was formed which was processed by various means depending on the device in which the test was carried out, i.e. either by a spatula if using an open plastic cup or by using two syringes of standard type (from, e.g., Becton, Dickinson & Co. (BD) or Qosina Corp.) connected to each other through the luer locks and pushing their content back and forth several times.

For simplicity, the first tests were made in disposable plastic cups, using an ordinary spatula in stainless steel. During mixing of the paste, the spatula was used to monitor the miscibility, and hence the ejectability through an imagined syringe. Later, the tests were developed and performed in syringes instead to better mimic the actual way of preparing and mixing the ready-to-use paste in the clinic, as well as to test the ejectability in a more accurate manner.

The evaluation comprised of observations of appearance, miscibility, consistency, ejectability, and time to thicken and solidify. All tests were performed at room temperature, at approximately 20-25° C.

Example 2

Diluent Test with Calcium Sulphate Hemihydrate

Presented in Table 2 and 3 are the data indicating that the Na-CMC (aq.) as diluent resulted in prolonged solidification time of $CaSO_4 \cdot \frac{1}{2}H_2O$. It is further apparent that by small changes to the concentration of Na-CMC the solidification time is easy to adjust. The Na-CMC used in this example is C9481 from Sigma-Aldrich (designated No. 1 in Table 1).

TABLE 2 reference examples

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 10.0 g $CaSO_4 \cdot \frac{1}{2}H_2O$ (Sigma-Aldrich) | 5.2 g 1.0% Na-CMC (aq.) | Plastic cup | Still possible to stir the paste after about 45 min | 5.2 | 5.2 |
| 2 | 10.0 g $CaSO_4 \cdot \frac{1}{2}H_2O$ (Sigma-Aldrich) | 5.0 g 1.0% Na-CMC (aq.) | Plastic cup | Started to thicken after 1.5 h | 5.0 | 5.0 |

TABLE 3

Compositions comprising 2.5 and 0.5 Na-CMC (mg)/Calcium sulphate (g)

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 10.0 g $CaSO_4 \cdot \frac{1}{2}H_2O$ (Sigma-Aldrich) | 5.0 g 0.5% Na-CMC (aq.) | Plastic cup | Still possible to stir after about 18 min, increase in viscosity after about 38 min | 2.5 | 2.5 |
| 2 | 10.0 g $CaSO_4 \cdot \frac{1}{2}H_2O$ (Sigma-Aldrich) | 5.0 g 0.1% Na-CMC (aq.) | Plastic cup | Thickened within 10 min, granular consistency | 0.5 | 0.5 |

One way of evaluating the ejectability of a composition comprised a 5 ml Plastipak syringe (BD), with a plastic stopper on the orifice side, containing 1.0 g of powder mix. To the powder mixture was then added the Na-CMC solution to be tested, normally about 0.8 ml, and the resulting mixture was stirred by hand using a plastic spatula until a homogeneous paste was formed. The piston was mounted and the plastic stopper removed. The paste was then gently ejected through the orifice of the syringe, by applying moderate hand force only. The time when the paste could not be ejected through the orifice was noted, even after applying higher forces. This is defined as the ejectability time. In addition, the time for the ejected paste, placed on a suitable flat surface covered with for example an Al foil, to solidify was noted. Every 30 second, a drop of paste was collected on the Al foil. When the 'drop' fractured upon loading, for example by pressing the fingertip, it was regarded as solid. This is defined as the solidification time. The thus determined solidification time should be from about 5 to about 15 min.

Example 3

Diluent Test with Calcium Sulphate Hemihydrate and Calcium Sulphate Dihydrate

The data in Table 4 and 5 below show the significant effect of Na-CMC (aq.) on the solidification rate of mixtures of $CaSO_4 \cdot 2H_2O$ and $CaSO_4 \cdot \frac{1}{2}H_2O$, and the correlation between solidification time and the concentration of Na-CMC. Compared to samples (No. 1 and 2 in Table 4) wherein MC+HAc or water is used as diluent, the solidification time is markedly increased.

From the results given in Table 4 it is also apparent that when $CaSO_4 \cdot 2H_2O$ is added to the powder mixture the solidification time becomes shorter compared to mixtures of only the hemihydrate form of calcium sulphate (see Table 2). The reason for this is that $CaSO_4 \cdot 2H_2O$ acts as crystal nuclei that speeds up the solidification rate.

The Na-CMC used in this example is C9481 from Sigma-Aldrich (designated No. 1 in Table 1).

TABLE 4 reference examples

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 3.33 g CaSO$_4$•2H$_2$O (Compactrol) + 6.68 g CaSO$_4$•½H$_2$O (Sigma-Aldrich) | 5.1 g H$_2$O | Plastic cup | Started to thicken within 1 min, impossible to eject after 1.5 min | — | — |
| 2 | 3.33 g CaSO$_4$•2H$_2$O (Compactrol) + 6.68 g CaSO$_4$•½H$_2$O (Sigma-Aldrich) | 5.0 g 1.0% MC + 1.0% HAc (aq.) | Plastic cup | Started to thicken within 1 min, judged as impossible to eject after 2 min | — | — |
| 3 | 3.33 g CaSO$_4$•2H$_2$O (Compactrol) + 6.68 g CaSO$_4$•½H$_2$O (Sigma-Aldrich) | 6.1 g 1.0% Na-CMC (aq.) | Plastic cup | Started to thicken and become grainy after 20 min. Not flowing after 29 min | 6.1 | 9.1 |
| 4 | 3.33 g CaSO$_4$•2H$_2$O (Compactrol) + 6.68 g CaSO$_4$•½H$_2$O (Sigma-Aldrich) | 5.0 g 1.0% Na-CMC (aq.) | Plastic cup | Started to become grainy after 11 min but judged as still ejectable, thickened after 22 min | 5.0 | 7.5 |

TABLE 5

Composition comprising 2.5 Na-CMC (mg)/Calcium sulphate (g)

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 3.33 g CaSO$_4$•2H$_2$O (Compactrol) + 6.68 g CaSO$_4$•½H$_2$O (Sigma-Aldrich) | 5.0 g 0.5% Na-CMC (aq.) | Plastic cup | Started to thicken and become grainy after 10 min. | 2.5 | 3.7 |

Example 4

Diluent Test with Calcium Sulphate Hemihydrate and Calcium Sulphate Dihydrate with a Pharmacologically Active Substance The results presented in Table 6 below demonstrate a concentration dependent effect of Na-CMC (aq.) on the solidification process of a powder formulation comprising both CaSO$_4$.2H$_2$O with a pharmacologically active substance, 2-hydroxyflutamide (2-HOF), and CaSO$_4$.½H$_2$O. In comparison, water and mixtures of HAc and MC gave rise to short solidification times.

The Na-CMC used in this example is C9481 from Sigma-Aldrich (designated No. 1 in Table 1).

TABLE 6

Compositions comprising 0.63-0.3 Na-CMC (mg)/Calcium sulphate (g)

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 1.33 g $CaSO_4 \cdot 2H_2O$ with 2-HOF[1] + 2.67 g $CaSO_4 \cdot \frac{1}{2}H_2O$ (Sigma-Aldrich) | 2.5 ml 0.1% Na-CMC (aq.) | Glass vial | Started to thicken after 6 min, solidified after about 12 min | 0.63 | 0.94 |
| 2 | 1.33 g $CaSO_4 \cdot 2H_2O$ with 2-HOF[1] + 2.67 g $CaSO_4 \cdot \frac{1}{2}H_2O$ (Sigma-Aldrich) | 2.5 ml 0.10% Na-CMC (aq.) | Glass vial | Started to thicken after 6 min, grainy after 10 min, solid after about 12 min | 0.63 | 0.94 |
| 3 | 1.33 g $CaSO_4 \cdot 2H_2O$ with 2-HOF[1] + 2.67 g $CaSO_4 \cdot \frac{1}{2}H_2O$ (Sigma-Aldrich) | 2.5 ml 0.05% Na-CMC (aq.) | Glass vial | Started to thicken after 3 min, solidified after about 6 min | 0.3 | 0.47 |

[1]The drug concentration was approximately 10 parts of 2-HOF to 100 parts of $CaSO_4 \cdot 2H_2O$ (~10/100), Powders were weighed and mixed in amber glass vials.

Example 5

Solidification Test for a High Viscosity Na-CMC

Presented in Table 7 are data on a sample of Na-CMC from Hercules (Blanose® 7H4F—No 11 from Table 1). This sample had the highest viscosity among all samples used. Blanose 7H4F has a viscosity of 5940 mPas and added to the composition in an amount of about 0.63 mg/g calcium sulphate the composition is still flowing after 15 minutes. Use of a similar concentration of C9481 (having a viscosity of 400-800 mPas) resulted in a composition that solidifies after about 12 minutes (see Table 5).

TABLE 7

Compositions comprising 0.63 Na-CMC (mg)/Calcium sulphate (g)

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 1.33 g $CaSO_4 \cdot 2H_2O$ with 2-HOF[1] + 2.67 g $CaSO_4 \cdot \frac{1}{2}H_2O$ (Sigma-Aldrich) | 2.5 ml 0.10% Blanose 7H4F (aq.) | Glass vial | Still flowing after 15 min, became grainy after 22 min and solid after 30 min | 0.63 | 0.94 |

[1]A mixture of compressed material left-over from previous preclinical testing; the drug concentration was approximately 10 parts of 2-HOF to 100 parts of $CaSO_4 \cdot 2H_2O$ (~10/100). Powders were weighed and mixed in amber glass vials at BMC, Uppsala.

Example 6

Ejectability of a Composition Comprising Calcium Sulphate Hemihydrate and Calcium Sulphate Dihydrate and a Pharmacologically Active Substance The results presented in Table 8 and 9 below show that it is possible to eject the paste through a thin cannula of 17 G when a drug concentration as high as 75/100 both in the compressed particles and the matrix were used.

The Na-CMC used was Blanose 7LF (No. 2 in Table 1).

The calcium sulphate hemihydrate labelled "CRVM" denotes a powder manufactured in the laboratory by heat treatment of calcium sulphate dihydrate. Calcium sulphate dihydrate from Carl Roth (>98%, Ph. Eur. reinst Carl Roth, Germany) was used as raw material. To prepare the powders, 250 g of calcium sulphate dihydrate is poured into a 2000 ml crystallisation basin. The crystallisation basin is kept in an oven at 200° C. for 4 hours. After cooling to room temperature outside the oven, the powder is transferred to a 1000 ml wide mouth bottle and suspended in 200 g of isopropanol. Grinding balls (64 pcs, 10 mm diameter) are added. A Turbula shaker-mixer is used to shake the wide mouth bottle for 24 h at 46 min$^{-1}$. After grinding, the grinding balls are removed and the slurry is poured into a 2000 ml crystallisation basin. The crystallisation basin is kept under a fume hood at room temperature until the isopropanol has evaporated completely. The regained powder is gently pressed through a 450 μm mesh sieve (for deagglomeration).

TABLE 8

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 (ref) | 0.17 g $CaSO_4 \cdot 2H_2O$ with 2-HOF[1] + 0.34 g $CaSO_4 \cdot \frac{1}{2}H_2O$ ('CRVM') with 2-HOF[2] | 0.31 ml water | 3 ml Plastipak syringe (BD) | Good miscibility in the syringe. Paste ejectable for 3 min, solidified after 4.5 min | — | |
| 2 | 0.17 g $CaSO_4 \cdot 2H_2O$ with 2-HOF[1] + 0.34 g $CaSO_4 \cdot \frac{1}{2}H_2O$ ('CRVM') with 2-HOF[2] | 1.14 ml 0.15% Blanose 7LF + 1.0% MC[3] (aq.) | 3 ml Plastipak syringe (BD) | Good miscibility in the syringe. Paste ejectable through a 17G × 17 cm cannula, solidified after 5 min | 3.4 | 5.03 |
| 3 | 0.17 g $CaSO_4 \cdot 2H_2O$ with 2-HOF[1] + 0.34 g $CaSO_4 \cdot \frac{1}{2}H_2O$ ('CRVM') with 2-HOF[2] | 0.31 ml 0.15% Blanose 7LF + 1.0% MC[3] (aq.) | 3 ml Plastipak syringe (BD) | Good miscibility in the syringe. Paste ejectable through a 17G × 17 cm cannula, solidified after 5 min | 0.9 | 1.4 |

[1]The drug concentration was 75 parts of 2-HOF to 100 parts of $CaSO_4 \cdot 2H_2O$ (75/100); 125-300 µm; Based on CRVM.
[2]Prepared in house. Drug concentration: 75 parts of 2-HOF per 100 parts of $CaSO_4 \cdot \frac{1}{2}H_2O$ (75/100).
[3]MC = methylcellulose (prepared by Apoteket AB)

TABLE 9

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 0.17 g $CaSO_4 \cdot 2H_2O$ with 2-HOF[1] + 0.34 g $CaSO_4 \cdot \frac{1}{2}H_2O$ ('CRVM') with 2-HOF[2] | 0.31 ml 0.30% Blanose 7LF (aq.) | 3 ml Plastipak syringe (BD) | Good miscibility in the syringe, paste ejectable for at least 20 min, also through a 17G × 17 cm cannula | 1.8 | 2.7 |

[1]The drug concentration was 75 parts of 2-HOF to 100 parts of $CaSO_4 \cdot 2H_2O$ (75/100); 125-300 µm; Based on CRVM.
[2]Prepared in house. Drug concentration: 75 parts of 2-HOF per 100 parts of $CaSO_4 \cdot \frac{1}{2}H_2O$ (75/100).

Example 7

Properties of Different Ratios of Calcium Sulphate Dihydrate and Calcium Sulphate Hemihydrate The results presented in Table 10 below indicate that a higher ratio of compressed $CaSO_4 \cdot 2H_2O$ particles to $CaSO_4 \cdot \frac{1}{2}H_2O$ (1:2→1:1) can be used when mixing with Na-CMC and ejecting the resulting paste through the orifice of the syringe used. These tests also indicate that diluent No. 8 in Table 1, based on Na-CMC of medium viscosity (Blanose 9M31XF) yielded an improved consistency of the resulting paste compared to that of the low-viscous diluent No. 2 from Table 1 (Blanose 7LF). Data also show that the solidification time was reduced in the presence of $CaSO_4 \cdot \frac{1}{2}H_2O$ without 2-HOF, from at least 20 min to less than 4 min.

TABLE 10

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 0.17 g $CaSO_4 \cdot 2H_2O$ with 2-HOF[1] + 0.34 g $CaSO_4 \cdot \frac{1}{2}H_2O$ ('CRVM') with 2-HOF[2] | 310 µl 0.30% Blanose 7LF (aq.) | 3 ml Plastipak syringe (BD) | Good miscibility in the syringe. Paste ejectable for at least 11 min | 1.8 | 2.7 |
| 2 | 0.25 g $CaSO_4 \cdot 2H_2O$ with 2-HOF[1] + 0.25 g $CaSO_4 \cdot \frac{1}{2}H_2O$ ('CRVM') with 2-HOF[2] | 310 µl 0.30% Blanose 7LF (aq.) | 3 ml Plastipak syringe (BD) | Good miscibility in the syringe. | 1.9 | 3.7 |
| 3 | 0.25 g $CaSO_4 \cdot 2H_2O$ with 2-HOF[1] + 0.25 g $CaSO_4 \cdot \frac{1}{2}H_2O$ ('CRVM') with 2-HOF[2] | 310 µl 0.30% Blanose 9M31XF (aq.) | 3 ml Plastipak syringe (BD) | Good miscibility in the syringe. Paste ejectable for at least 10 min. | 1.9 | 3.7 |
| 4 | 0.25 g $CaSO_4 \cdot 2H_2O$ with 2-HOF[1] + 0.25 g $CaSO_4 \cdot \frac{1}{2}H_2O$ ('CRVM') without 2-HOF[3] | 310 µl 0.30% Blanose 9M31XF (aq.) | 3 ml Plastipak syringe (BD) | Good miscibility in the syringe. | 1.9 | 3.7 |

[1]The drug concentration was 75 parts of 2-HOF to 100 parts of $CaSO_4 \cdot 2H_2O$ (75/100); 125-300 µm; Based on CRVM.
[2]Prepared in house. Drug concentration: 75 parts of 2-HOF per 100 parts of $CaSO_4 \cdot \frac{1}{2}H_2O$ (75/100).
[3]Prepared in house.

Example 8

Properties of Different Rations of Calcium Sulphate Dihydrate and Calcium Sulphate Hemihydrate The results presented in Table 11 below confirm that a higher ratio of compressed $CaSO_4 \cdot 2H_2O$ particles to $CaSO_4 \cdot \frac{1}{2}H_2O$ (1:2→1:1) can be used when mixing with the Na-CMC and ejecting the resulting paste through the orifice of the syringe used, but also through a cannula. These tests also confirm that diluent No. 8 from Table 1, based on Na-CMC of medium viscosity, yielded an acceptable consistency of the resulting paste. Data also show that a decrease in concentration from 0.30% to 0.25% resulted in a quicker solidification, since the paste was impossible to eject through the cannula after about 7 min.

TABLE 11

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| 1 | 0.51 g $CaSO_4 \cdot 2H_2O$ with 2-HOF[1] + 0.26 g $CaSO_4 \cdot \frac{1}{2}H_2O$ ('CRVM') with 2-HOF[2] + 0.27 g $CaSO_4 \cdot \frac{1}{2}H_2O$ ('CRVM') without 2-HOF[3] | 625 µl 0.30% Blanose 9M31XF (aq.) | 5 ml Plastipak syringe (BD) | Good miscibility in the syringe. Paste easily ejectable | 1.8 | 3.5 |
| 2 | 0.33 g $CaSO_4 \cdot 2H_2O$ with 2-HOF[1] + 0.33 g $CaSO_4 \cdot \frac{1}{2}H_2O$ ('CRVM') | 625 µl 0.30% Blanose 9M31XF (aq.) | 5 ml Plastipak syringe (BD) | Good miscibility in the syringe. | 1.9 | 2.8 |

TABLE 11-continued

| No. | Powder | Diluent | Mixing device | Observations | Na-CMC (mg)/total calcium sulphate (g) | Na-CMC (mg)/calcium sulphate hemihydrate (g) |
|---|---|---|---|---|---|---|
| | with 2-HOF[2] + 0.33 g $CaSO_4 \cdot \frac{1}{2}H_2O$ ('CRVM') without 2-HOF[3] | | | | | |
| 3 | 0.33 g $CaSO_4 \cdot 2H_2O$ with 2-HOF[1] + 0.33 g $CaSO_4 \cdot \frac{1}{2}H_2O$ ('CRVM') with 2-HOF[2] + 0.33 g $CaSO_4 \cdot \frac{1}{2}H_2O$ ('CRVM') without 2-HOF[3] | 0.78 g 0.30% Blanose 9M31XF (aq.) | 5 ml Plastipak syringe (BD) | Good miscibility in the syringe. Paste ejectable for at least 15 min through a 17G × 17 cm cannula | 2.3 | 3.5 |
| 4 | 0.50 g $CaSO_4 \cdot 2H_2O$ with 2-HOF[1] + 0.25 g $CaSO_4 \cdot \frac{1}{2}H_2O$ ('CRVM') with 2-HOF[2] + 0.25 g $CaSO_4 \cdot \frac{1}{2}H_2O$ ('CRVM') without 2-HOF[3] | 0.71 g 0.30% Blanose 9M31XF (aq.) | 5 ml Plastipak syringe (BD) | Good miscibility in the syringe. Paste ejectable up to 30 min through a 17G × 17 cm cannula | 2.1 | 4.3 |
| 5 | 0.50 g $CaSO_4 \cdot 2H_2O$ with 2-HOF[1] + 0.25 g $CaSO_4 \cdot \frac{1}{2}H_2O$ ('CRVM') with 2-HOF[2] + 0.25 g $CaSO_4 \cdot \frac{1}{2}H_2O$ ('CRVM') without 2-HOF[3] | 0.70 g 0.25% Blanose 9M31XF (aq.) | 5 ml Plastipak syringe (BD) | Good miscibility in the syringe. Paste ejectable up to 7 min through a 17G × 17 cm cannula | 1.75 | 3.5 |

[1]The drug concentration was 75 parts of 2-HOF to 100 parts of $CaSO_4 \cdot 2H_2O$ (75/100); 125-300 µm; Based on CRVM.
[2]Prepared in house. Drug concentration: 75 parts of 2-HOF per 100 parts of $CaSO_4 \cdot \frac{1}{2}H_2O$ (75/100).
[3]Prepared in house.

Example 9

Properties of Different Ratios of Calcium Sulphate Dihydrate and Calcium Sulphate Hemihydrate and Na-CMC with Respect to Ejectability To study the effects of Na-CMC on the rheological properties of the paste, without being disturbed by the hydration (the continuous thickening) of the past, an experiment was performed by mixing and investigating the ejectability with non-solidifying calcium sulphates. Both calcium sulphate dehydrate and anhydrous calcium sulphate have this property. What is clearly seen is that there is a dispersion effect of Na-CMC is that for comparable pastes made with CMC or MC, the CMC pastes are more flowably (less viscous). This increased flowability appears after some mixing of the paste. The test include ejectability with syringes, in some cases with cannula. The most problematic part of ejectability is to make the paste exit the syringe and transfer from the wide syringe body to the much narrower syringe exit is the most complicated part of ejection.

The tests were performed to evaluate the suitability of different diluents for the preparation of injectable calcium sulphate pastes. Non-hydrating calcium sulphate powders were used to exclude the effects of curing, as experienced with calcium sulphate hemihydrate, on the study of the handling properties of the pastes.

Three calcium sulphate materials were used in the tests:
1. Calcium sulphate dihydrate: Fluka, Product No. 21 246;
2. Calcium sulphate dihydrate: Compactrol, Batch 06021C;
3. Calcium sulphate (anhydrous): Sigma-Aldrich, Product No. 237132. It should be noted that calcium sulphate anhydrous cannot be hydrated and thus behaves analogously to dihydrate in the sense that mixture containing only anhydrous calcium sulphate does not cure.

Two aqueous diluents were tested and compared to pure deionised water:
1. 0.25% (w/w) Na-CMC;
2. 0.44% (w/w) methylcellulose (MC).

Water or aqueous solution of cellulose ether was added to the dry calcium sulphate powder and the mixture was vigorously stirred by a spatula. Some slurries were also treated in an ultrasonic bath at elevated temperature (about 40° C.) for a less than 1 min after which the appearance of the slurry was noted.

Some of the resulting slurries were transferred to a 10 ml syringe, in some cases with a cannula (1.65/1.40×149 mm). The results are summarised in Table 12 below.

TABLE 12

| No. | Powder | Diluent | Result |
|---|---|---|---|
| 18 | 4.01 g of CaSO$_4$ anhydrous + 3.02 g of granulated material* | 3.99 g of deionised H$_2$O | Viscous slurry; difficult to eject through the Luer orifice of a 10 ml syringe |
| 19 | 4.00 g of CaSO$_4$ anhydrous + 3.01 g of granulated material* | 4.01 g of 0.25% Na-CMC (aq.) | Less viscous, more runny slurry than in 18; ejectable through Luer of a 10 ml syringe, also with cannula. |
| 20 | 4.01 g of CaSO$_4$ anhydrous + 3.02 g of granulated material* | 4.00 g of 0.44% MC (aq.) | Viscous slurry which stabilises air bubbles; difficult to eject through the Luer orifice of a 10 ml syringe |
| 21 | 7.00 g of CaSO$_4$•2H$_2$O (Fluka) | 4.35 g of deionised H$_2$O | Viscous slurry. In general ejectable through the orifice of a 10 ml syringe |
| 22 | 7.00 g of CaSO$_4$•2H$_2$O (Fluka) | 4.35 g of 0.25% Na-CMC (aq.) | Less viscous, more runny slurry than in 21. Ejectability as in 21 |
| 23 | 7.01 g of CaSO$_4$•2H$_2$O (Fluka) | 4.35 g of 0.44% MC (aq.) | Thicker slurry than in 21. Stabilises air bubbles. Ejectability as in 21 |
| 24 | 7.01 g of CaSO$_4$ anhydrous | 4.37 g of deionised H$_2$O | Viscous slurry. Ejectable through the Luer of a 10 ml syringe, also with cannula |
| 25 | 7.01 g of CaSO$_4$ anhydrous | 4.34 g of 0.25% Na-CMC (aq.) | Less viscous, more runny slurry than in 24. Ejectability as in 24 |
| 26 | 7.01 g of CaSO$_4$ anhydrous | 4.35 g of 0.44% MC (aq.) | Viscous slurry, thicker than in 24. Slurry holds air bubbles. Ejectability as in 24 |
| A | 7.00 g of CaSO$_4$•2H$_2$O (Compactrol) | 4.35 g of deionised H$_2$O | Viscous slurry. Ejectable through the Luer of a 10 ml syringe. |
| B | 7.00 g of CaSO$_4$•2H$_2$O (Compactrol) | 4.36 g of 0.25% Na-CMC (aq.) | Less viscous, more runny slurry. Ejectable through the Luer of a 10 ml syringe. |
| C | 7.00 g of CaSO$_4$•2H$_2$O (Compactrol) | 4.37 g of 0.44% MC (aq.) | Viscous slurry. Ejectable through the Luer of a 10 ml syringe. Holds air bubbles. |
| D | 7.00 g of CaSO$_4$•2H$_2$O (Compactrol) | 3.95 g of deionised H$_2$O | Toothpaste-like slurry. Difficult to eject through the Luer of a 10 ml syringe. Blocks often. |
| E | 7.00 g of CaSO$_4$•2H$_2$O (Compactrol) | 3.95 g of 0.25% Na-CMC (aq.) | Less thick slurry than in D. Ejectable through the Luer of a 10 ml syringe. Rarely blocks. |
| F | 7.00 g of CaSO$_4$•2H$_2$O (Compactrol) | 3.95 g of 0.44% MC (aq.) | Thick slurry. Difficult to eject through the Luer orifice of a 10 ml syringe. Stabilises air bubbles strongly. |

*Densified grains, 125-300 μm, of CaSO$_4$•2H$_2$O and 2-HOF.

Some of these (D, E, F) thus experiment simulates the conditions appearing when the ready-to-use composition is reaching its solidification point or partial solidification during the end of the injection procedure.

It is shown in earlier experiments that the aqueous Na-CMC solutions very efficiently retard the hydration of calcium sulphate hemihydrates. Solutions of MC lacks this property.

Surprisingly, as shown by these experiments, besides being a very efficient retarding agent for the setting of calcium sulphate hemihydrate, an aqueous solution of Na-CMC is also a very efficient dispersing agent. By means of the addition of Na-CMC (aq.), the transformation of the powder into a slurry and its subsequent ejection are facilitated.

The non-ionic cellulose ether MC is inferior to Na-CMC in all aspects; it is a bad dispersing agent, it stabilises air bubbles, and it does not retard the hardening (of calcium sulphate hemihydrate; not shown here).

As seen herein, Na-CMC thus provides a suitable rheological property to an aqueous suspension of CaSO$_4$ paste and inhibits sedimentation and caking.

The invention claimed is:

1. A kit comprising:
   1) a first component consisting of:
      (a) calcium sulphate hemihydrate, and
      (b) compressed calcium sulphate dihydrate particles, and wherein one or more pharmaceutically active substances are present in (a) or (b), or both in (a) and (b), and ii) a second component consisting of:
  (c) sodium carboxymethylcellulose (Na-CMC) dissolved in water, wherein the ratio R of sodium carboxymethylcellulose to calcium sulphate in the kit is from 0.1 mg sodium carboxymethylcellulose (calculated as Na-CMC)/g calcium sulphate to 4 mg sodium carboxymethylcellulose (calculated as Na-CMC)/g calcium sulphate.

2. The kit according to claim 1, wherein the ratio R is from 0.5 mg sodium carboxymethylcellulose (calculated as Na-CMC)/g calcium sulphate hemihydrate to 3 mg sodium carboxymethylcellulose (calculated as Na-CMC)/g calcium sulphate hemihydrate.

3. The kit according to claim 1, wherein the ratio R is from 1 mg sodium carboxymethylcellulose (calculated as Na-CMC)/g calcium sulphate hemihydrate to 3 mg sodium carboxymethylcellulose (calculated as Na-CMC)/g calcium sulphate hemihydrate.

4. The kit according to claim 1, wherein the concentration of sodium carboxymethylcellulose in water is from 0.05% w/w to 1% w/w.

5. A kit comprising:
  i) a first component consisting of:
    (a) calcium sulphate hemihydrate, and
    (b) compressed calcium sulphate dihydrate particles, and
    (c) optionally one or more pharmaceutically active substances; and
  ii) a second component consisting of:
    (d) sodium carboxymethylcellulose (Na-CMC) dissolved in water, wherein the ratio R of sodium carboxymethylcellulose to calcium sulphate in the kit is from 0.1 mg sodium carboxymethylcellulose (calculated as Na-CMC)/g calcium sulphate to 4 mg sodium carboxymethylcellulose (calculated as Na-CMC)/g calcium sulphate, and
    (e) optionally one or more pharmaceutically active substances; and wherein the one or more pharmaceutically active substances are present in the first component or the second component, or in both the first and the second components.

6. The kit according to claim 5, wherein the one or more pharmaceutically active substances is an antiandrogen.

7. The kit according to claim 6, wherein the one or more pharmaceutically active substances is cyproteron, flutamide, or 2-hydroxyflutamide.

8. The kit according to claim 1, wherein the compressed particles of calcium sulphate dihydrate comprise the one or more pharmaceutically active substances.

9. The kit according to claim 1, wherein the calcium sulphate hemihydrate of component i) is present in admixture with the one or more pharmaceutically active substances.

10. A ready-to-use composition consisting of an admixture of the first component i) and the second component ii) as defined in claim 1.

11. The kit according to claim 1, wherein said calcium sulphate hemihydrate is in the form of a powder with a mean grain size of at the most 75 μm.

12. The kit according to claim 1, wherein said calcium sulphate dihydrate has a particle size from 50 to 600 μm.

13. The kit according to claim 1, wherein the concentration of said one or more active substances is in a range from 0.01% w/w to 75% w/w based on the total weight of the component in which the one or more pharmaceutically active substances is present.

14. The kit according to claim 1, wherein said carboxymethylcellulose has a degree of substitution from 0.60 to 0.95 derivatives per monomer unit, and/or a viscosity from 40 to 7000 mPas, at 20° C. and normal pressure.

15. The ready-to-use composition according to claim 10, wherein the ready-to-use composition is ejectable through the orifice of a syringe.

16. The ready-to-use composition according to claim 15, wherein said syringe is equipped with a cannula or needle of 15-17 G or smaller.

17. The kit of claim 5, wherein the pharmaceutically active substance is a therapeutically active substance.

18. The kit of claim 5, wherein the pharmaceutically active substance is prophylactically active substance.

19. The kit of claim 5, wherein the pharmaceutically active substance is diagnostically active substance.

20. The kit of claim 1, wherein the pharmaceutically active substance is a therapeutically active substance.

21. The kit of claim 1, wherein the pharmaceutically active substance is prophylactically active substance.

22. The kit of claim 1, wherein the pharmaceutically active substance is diagnostically active substance.

23. A kit consisting of:
  i) a first component consisting of:
    (a) calcium sulphate hemihydrate, and
    (b) compressed calcium sulphate dihydrate particles, and
    (c) optionally one or more pharmaceutically active substances; and
  ii) a second component consisting of:
    (d) sodium carboxymethylcellulose (Na-CMC) dissolved in water, wherein the ratio R of sodium carboxymethylcellulose to calcium sulphate in the kit is from 0.1 mg sodium carboxymethylcellulose (calculated as Na-CMC)/g calcium sulphate to 4 mg sodium carboxymethylcellulose (calculated as Na-CMC)/g calcium sulphate, and
    (e) optionally one or more pharmaceutically active substances; and wherein the one or more pharmaceutically active substances are present in the first component or the second component, or in both the first and the second components.

* * * * *